United States Patent [19]

Kunstmann et al.

[11] 4,118,497
[45] Oct. 3, 1978

[54] ANTIDEPRESSANTLY ACTIVE 5-(4-AMINOPHENYL)-HEXAHYDRO-1H-INDENO-(1,2-B)PYRIDINE

[75] Inventors: Rudolf Kunstmann, Breckenheim; Ulrich Lerch; Hermann Gerhards, both of Hofheim, Taunus, all of Fed. Rep. of Germany

[73] Assignee: Hoechst Aktiengesellschaft, Frankfurt am Main, Fed. Rep. of Germany

[21] Appl. No.: 649,638

[22] Filed: Jan. 16, 1976

[30] Foreign Application Priority Data

Jan. 18, 1975 [DE] Fed. Rep. of Germany ....... 2501930

[51] Int. Cl.$^2$ ................. C07D 221/16; A61K 31/445
[52] U.S. Cl. ............................. 424/267; 260/293.54; 260/293.78; 260/293.84; 260/465 E; 260/465 G; 260/570.8 R

[58] Field of Search .................... 260/293.54; 424/267

[56] References Cited

U.S. PATENT DOCUMENTS

| | | | |
|---|---|---|---|
| 3,408,353 | 10/1968 | Jucker et al. | 260/293 |
| 3,678,057 | 7/1972 | Ebnöther et al. | 260/293.54 |
| 3,839,338 | 10/1974 | Albertson et al. | 260/287 R |
| 3,898,235 | 8/1975 | Albertson et al. | 260/283 R |

Primary Examiner—Henry R. Jiles
Assistant Examiner—Richard A. Schwartz
Attorney, Agent, or Firm—Curtis, Morris & Safford

[57] ABSTRACT

The invention relates to hexahydro-1H-indeno/1,2-b/pyridines and a process for their manufacture. These compounds and the physiologically tolerable salts thereof are useful as agents for the treatment of psychic diseases.

3 Claims, No Drawings

ANTIDEPRESSANTLY ACTIVE 5-(4-AMINOPHENYL)-HEXAHYDRO-1H-INDENO-(1,2-B)PYRIDINE

The present invention relates to hexahydro-1H-indeno[1,2-b]pyridines and a process for their manufacture.

Isomeric pairs of 5-phenyl-2,3,4,4a,5,9b-hexahydro-1H-indeno[1,2-b]pyridine are disclosed in J. Med. Chem. 15, 466 (1972) as standards to examine structure-activity-relationships. Furthermore, U.S. Pat. No. 3,639,411 describes compounds which can be used as intermediates in the synthesis of hexahydro-1H-indeno[1,2-b]pyridines which may carry two substituents, i.e. alkyl or phenyl, which may be identical or different, in the 5-position.

Hexahydro-1H-indeno[1,2-b]pyridines which are monosubstituted in the 5-position by an aromatic group or a heterocyclic group have been synthesized and found to possess high psychotropic activity.

Specifically, this invention relates to hexahydro-1H-indeno[1,2-b]pyridines of formula I

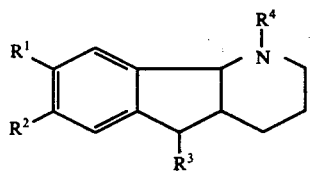

in which
- $R^1$ and $R^2$ are identical or different, each representing hydrogen, halogen, hydroxy or an alkyl or alkoxy group having 1 to 6 carbon atoms,
- $R^3$ stands for a benzene radical which is mono or disubstituted by halogen, a hydroxy, nitro or an amino group or by an amino group substituted by one or two aliphatic, cycloaliphatic or aromatic hydrocarbon radicals having 2 to 18 carbon atoms, in which case the nitrogen atom may be part of a heterocyclic ring, or by an acylamino, an alkyl or alkoxy group each having 1 to 6 carbon atoms or by a trifluoromethyl group, or $R^3$ stands for the pyridine or thiophene radical and, if at least one of the radicals $R^1$, $R^2$ and $R^4$ is not hydrogen, $R^3$ also stands for the benzene radical,
- $R^4$ stands for hydrogen or a saturated or unsaturated, straight-chain or branched aliphatic or saturated or unsaturated cycloaliphatic or cycloaliphatic-aliphatic hydrocarbon radical having 1 to 6 carbon atoms.

The invention also relates to the physiologically acceptable salts of these compounds.

The invention especially relates to compounds in which $R^1$ and $R^2$ are identical and each stands for hydrogen or an alkoxy group having 1 to 4 carbon atoms or $R^1$ is hydrogen and $R^2$ is hydroxyl, halogen or an alkoxy group having 1 to 6 carbon atoms, $R^3$ stands for the pyridyl, thienyl or phenyl ring which is substituted by halogen, a hydroxy, amino, trifluoromethyl, acylamino, alkoxy or alkyl group having 1 to 6 carbon atoms, or a phenyl ring which is disubstituted by a combination of halogen and an amino or acylamino group having 1 to 4 carbon atoms, and $R^4$ stands for hydrogen or a saturated or unsaturated straight-chain or branched aliphatic or cycloaliphatic or cycloaliphaticaliphatic hydrocarbon radical having 1 to 6 carbon atoms.

Compounds in which $R^1$ and $R^2$ are identical and each stands for hydrogen or the methoxy group or $R^1$ is hydrogen and $R^2$ is chlorine, hydroxyl, the methyl or methoxy group, $R^3$ stands for the pyridyl, thienyl or phenyl ring which is substituted by chlorine, fluorine, a hydroxy, amino, acetylamino, methyl methoxy or trifluoromethyl group, or a phenyl ring which is disubstituted by a combination of chlorine and an amino or acetylamino group, and $R^4$ is hydrogen, the methyl or propargyl group, are of spatial interest.

If $R^3$ stands for the phenyl ring, the compounds related to in this invention are especially those in which $R^1$ and $R^2$ are identical and each is an alkoxy group having 1 to 4 carbon atoms, the methoxy group being especially preferred, or $R^1$ is hydrogen and $R^2$ is chlorine, the methyl, methoxy or hydroxy group and $R^4$ is hydrogen, a straight-chain, branched, saturated or unsaturated aliphatic hydrocarbon radical having 1 to 4 carbon atoms, the hydrogen, methyl or propargyl substituent being preferred.

This invention further relates to processes for the manufacture of these compounds and to pharmaceutical preparations thereof.

The process for the manufacture of the compounds of formula I comprises (a) reducing compounds of formula II

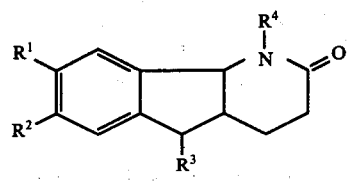

(b) cyclizing compounds of formula III while splitting off HX

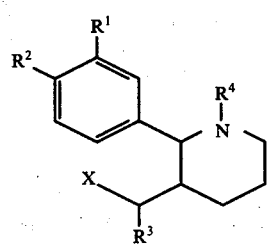

(c) hydrogenating compounds of formula IV a or IV b

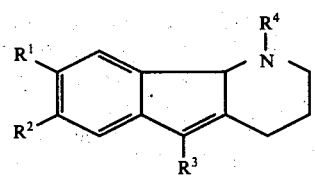

-continued

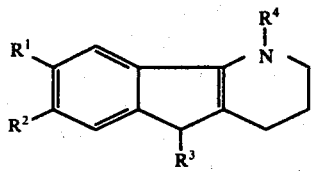  IVb (d) cyclizing compounds of formula V

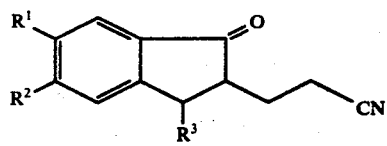  V under reductive conditions in presence of the corresponding amine $R^4 — NH_2$, (e) cyclizing compounds of formula VI

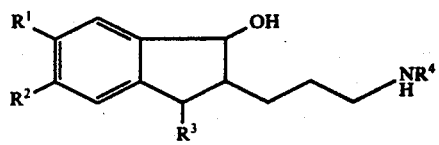  VI while water is split off, (f) introducing the substituent $R^4$ by alkylation into compounds of formula VII

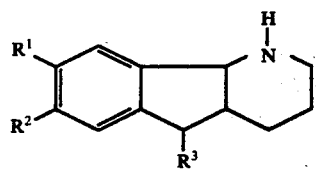  VII (g) introducing the substituents $R^1$ and $R^2$ into compounds of formula VIII

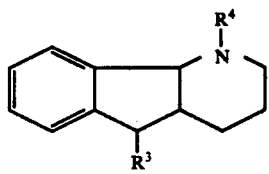  VIII (h) substituting the phenyl ring subsequently if $R^3$ is the phenyl ring,
(i) modifying a radical $R^1$, $R^2$, $R^4$ or substituents optionally present at the phenyl ring in 5-position in such a manner that further compounds of formula I are obtained or
(k) epimerizing the position of $R^3$ in compounds of formula I.

Preparation of the starting compounds of formula II for method a) is described in German Offenlegungsschrift No. 2,325,581. Generally, they are prepared by reacting a γ-benzoyl-butyric acid nitrile IX in an acidic medium with an aldehyde X and then hydrogenating the double bond in 4a,5-position of compound XI to obtain compound XII.

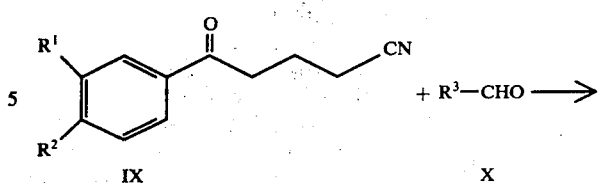

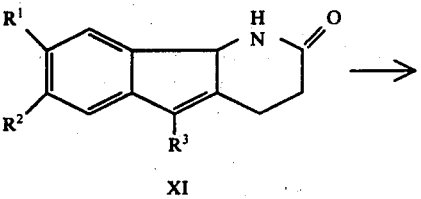  XI

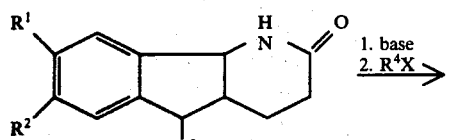  XII

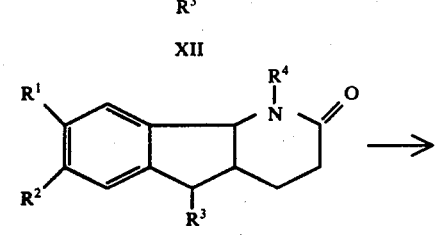  II

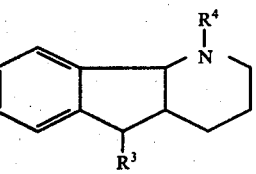  I

The compounds XII are alkylated at the nitrogen atom in usual manner, the amide being deprotonized with a base in a suitable solvent, and then reacting it with the corresponding alkyl halide. Deprotonization can be effected, for example, by an alkali metal amide, such as $NaNH_2$, in inert solvents, such as benzene or toluene (for example, as described in Org. Synth. 25, 25 (1945)) or also by sodium hydride in dimethyl sulfoxide. It is also possible with the use of alkali metal hydroxides, such as KOH, in polar solvents, such as dimethyl sulfoxide or dimethyl formamide (cf. Synthesis (1971), 266). The temperature required for deprotonization and subsequent alkylation depends on the base, the solvent and the alkylating agent chosen and can be varied within wide limits, that is to say between $-20°$ C and the boiling point of the solvent.

Reduction of compounds II to compounds I is most simply effected with the aid of a complexed metal hydride, for example lithium aluminum hydride or a metal hydride, for example diisobuutyl aluminum hydride, in inert solvents, for example diethyl ether, tetrahydrofurane or a mixture of these solvents, at a temperature ranging between room temperature and the boiling point of the solvent. The best is to refer to Org. Syn. Coll. Vol. 4, 355 (1963).

Preparation of the starting compounds III (X=OH) which are required for method b) is described in U.S. Pat. No. 3,639,411. They are prepared by acylating a 2-cyanoethylmalonic ester XIII in presence of suitable bases, for example NaH in toluene with the corresponding benzoyl halide. Acylation takes place already at very low temperatures, advantageously from −20° C to room temperature. Compounds XIV are obtained which are then hydrogenated to yield compounds XV, the catalyst to be used being Ni or noble metal catalysts, for example Pd, Pt, Rh, which may be on carrier materials, for example barium carbonate, active charcoal, or kieselguhr and different solvents may be used, for example water, alcohols, for example methanol or ethanol, ethers, for example dimethoxyethane or tetrahydrofurane, polar solvents, for example dimethyl formamide or solvent mixtures. The reaction can be accelerated by varying the temperature between room temperature and 150° C and by increasing the pressure from atmospheric pressure to 150 atm. at maximum.

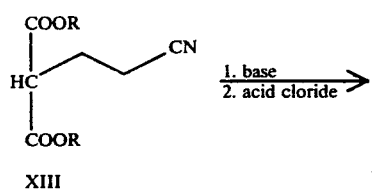

XIII

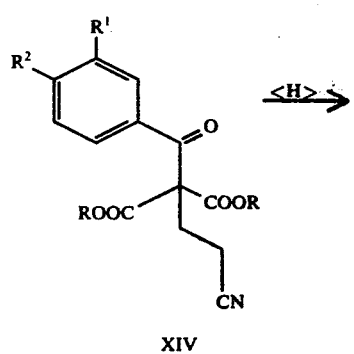

XIV

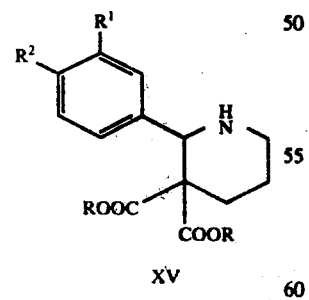

XV

By partial saponification of the malonic diester of formula XV with an equimolar amount of a base, for example KOH in ethanol at room temperature, subsequent isolation of the semi-ester of formula XVI, and distillation of the crude semi-ester compound XVII is obtained.

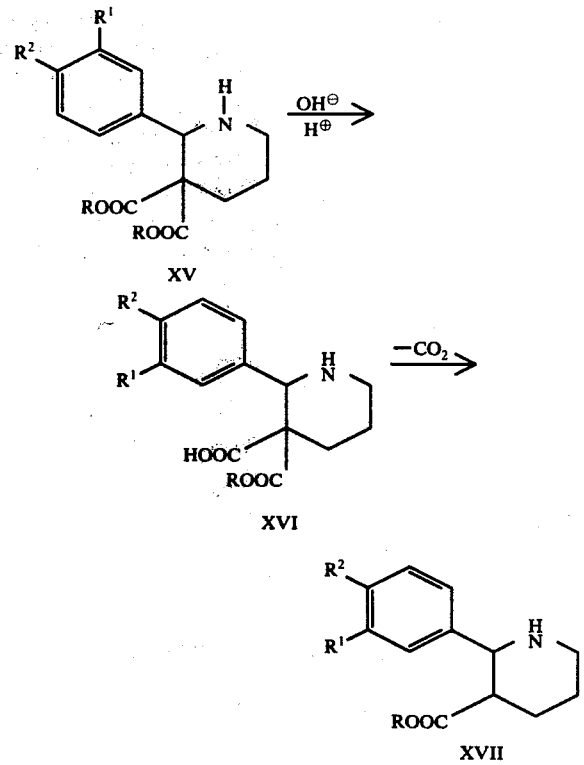

The same compounds (XVII) are obtained when the compounds XVIII obtained as intermediates in the preparation of the γ-benzoylbutyric acid nitriles of formula IX are subjected to a hydrogenation comparable to the one described for compound XIV.

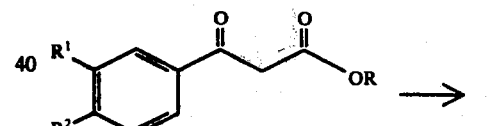

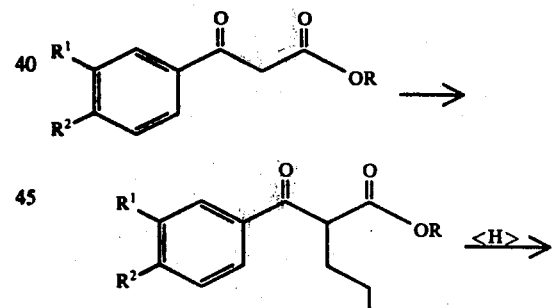

The compounds of formula XVII can now be converted by various methods into compounds of formula I. In following method b), the compounds of formula XVII are saponified according to one of the usual methods to an acid and the acid is reacted to the acid chloride. The acid chlorides of formula XIX can now be converted by various methods into the ketones XXI, either according to Liebig's Ann. Chem. 655, 90 (1962) or Angew. Chem. Int. Ed. 1, 351 (1962), by reacting the acid chloride in suitable inert solvents, for example diethyl ether, tetrahydrofurane, toluene or pentane, with or without the addition of a base, for example triethyl amine or pyridine, with imidazole at a temperature ranging from −20° C to 120° C to form the corresponding n-acylimidazole XX, and subjecting that N-acylimidazole to a generally employed Grignard reaction with R³—Mg—X, whereupon the ketones XXI are obtained in smooth reaction,

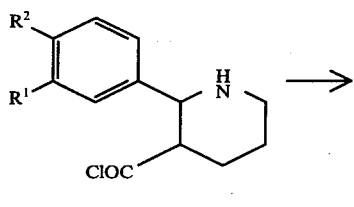

XIX

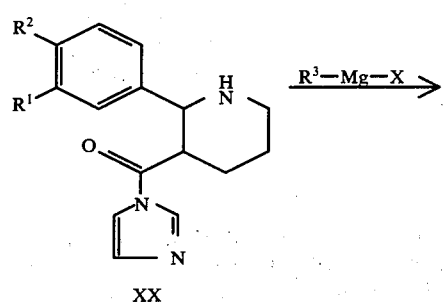

XX or by following the method described in Org. Synth. Coll. Vol. 3, 601, according to which the Grignard reactant, prepared from the halide R³X (X = Cl, Br, I) and magnesium, is reacted with cadmium chloride at elevated temperature to form the cadmium organic compound CdR₂³ and this compound is reacted with the acid chloride to form a ketone of formula XXI. Suitable solvents are inert solvents, for example diethyl ether dioxane, tetrahydrofurane, dimethoxy ethane, suitable temperatures being within the range of room temperature and the boiling point of the solvent.

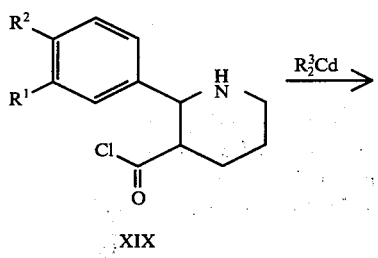

XIX

-continued

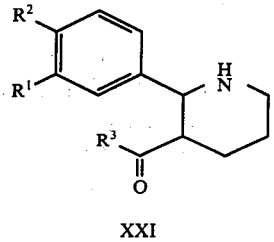

XXI

Further possibilities for the conversion of acid chlorides into ketones are described in Organic React. 8, 28 (1954) and in a complete summary by J. T. Harrison, S. Harrison Compendium of Organic Synthetic methods, Wiley Interscience, New York, London, Sydney, Toronto, 1971.

In method b), commpounds XXI are reduced to the corresponding alcohols III (X = OH). The reaction may be carried out by working in the presence of Ni or noble metal catalysts, for example Pd or Pt, with or without a carrier material, for example barium carbonate, active charcoal or kieselguhr at a temperature between room temperature and 150° C and under pressures between atmospheric pressure and 150 atm. in a suitable solvent, for example water or alcohols, for example methanol, iso-propanol or ethers, for example diethyl ether, terahydrofurane or polar solvents, for example glacial acetic acid or dimethyl formamide. The corresponding alcohols III (X = OH) are obtained in quantitative yield.

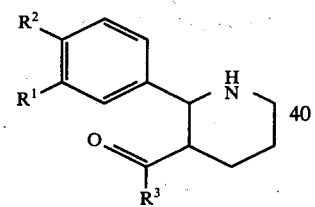

XXI

III

Reduction of compounds XXI to compounds III (X = OH) may also, in general, be carried out with complex hydrides, for example LiAlH₄, NaBH₄, LiBH₄, (iso-C₄H₉)₂, AlH, Zn (BH₄)₂, suitable solvents to be worked in with respect to the specific reduction agent used being, for example water, alcohols, for example methanol, ethanol, ethers, for example dimethoxy ethane, diethyl ether, tetrahydrofurane, or aromatic, aliphatic or cycloaliphatic hydrocarbons, for example benzene, toluene, pentane or cyclohexane and the suitable temperature being room temperature up to the boiling point of the solvent.

The alcohols III (X = OH) can now be converted in known manner into derivatives, for example p-toluenesulfonyl or methane sulfonyl derivatives, acetates or into halides, for example chlorides or bromides, all of which may be subjected to the reaction conditions for cyclization mentioned below.

The compounds III so obtained are now converted according to method b) into the compounds I with the aid of acid catalysts, for which may especially be mentioned mineral acids, for example sulfuric acid, hydrochloric acid and phosphoric acid, or Lewis acids, for example boron trifluoride, aluminum chloride and phosphorus oxychloride. Suitable solvents, if employed, are especially, for example water, benzene, toluene, chlorobenzene, carbon tetrachloride or trichloroethylene. The preferred temperatures are within the range of room temperature and 180° C.

The preparation of the starting compounds IV a, b required for method c is described hereinbefore. When ketones XXI are subjected to a cyclization reaction with acid catalysts, as is described for method b), compounds IV a, b are obtained in a smooth reaction. The position of the double bonds cannot precisely be defined.

Compounds IV a, b can also be prepared on the basis of esters. When compounds XVII are treated with acid catalysts under conditions that are described for method b), compounds XXII are obtained in almost quantitative yield. When compounds XXII are reacted with the Grignard reactant prepared from $R^3$-X and Mg in an inert solvent, for example diethyl ether or triethyl amine, alcohols of the formula XXIII are obtained which are dehydrated by acid catalysts, for example mineral acids, such as sulfuric acid or hydrochloric acid, to compounds I ($R^4 = H$).

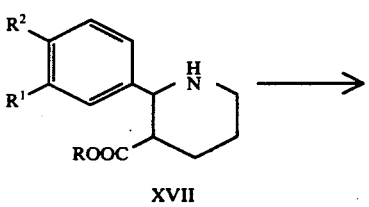

XVII

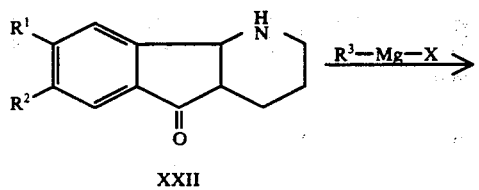

XXII

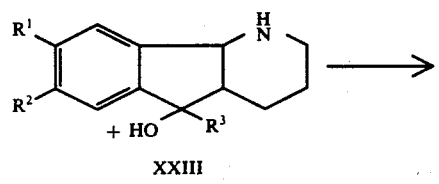

XXIII

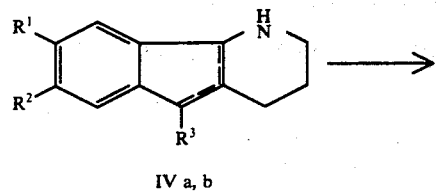

IV a, b

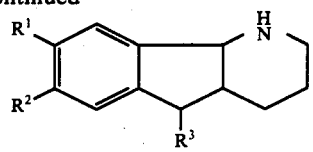

I ($R^4 = H$)

Hydrogenation of the compounds IV (a,b) according to method c) is performed under conditions similar to those indicated for the conversion of compounds XXI into compounds III (X = OH). If catalysts are used, Raney-Nickel in ethanol or methanol and optionally the addition of dimethyl formamide is advantageous, if temperatures within the range of room temperature and 80° C and pressures within the range of 1 atmosphere to 80 atmospheres are employed.

The radical $R^4$ can be introduced into compounds of formula XVII at the nitrogen atom as well as into prior or later intermediates such as are described in methods b) and c) and serving in the preparation of compounds III and IV a, b, which is to be described in method f), so that the methods b) and c) described hereinbefore refer to every compound of formula I.

For reason of a better handling of the individual reaction steps described in methods b) and c), the secondary amine can be protected by a suitable protecting group. For this purpose, a reaction with chloroformiate leading to the urethane and carried out according to the methods generally used, or also a benzylation according to the usual methods, is suitable. The protecting groups are split off according to the methods usually employed: in case of the urethane it is eliminated hydrolytically, whereas the benzyl group is removed hydrogenolytically.

The compounds V, which are used as starting materials according to method d), are prepared by starting from the corresponding indanone derivatives XXIV, which are prepared according to one of the usual methods and are then subjected to a cyanoethylation reaction (cf. J. Chem. Soc. (1956), 959).

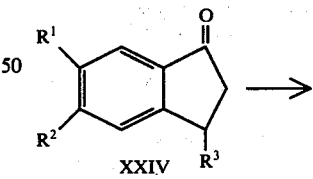

XXIV

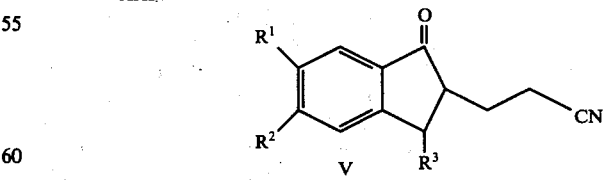

V

A new method for the preparation of 3-(indane-1-one-2-yl)-propionic acids and their derivatives start from compounds of formula XI. When these compounds XI are saponified under acid or alkaline conditions, the corresponding propionic acids XXV are obtained in quantitative yield.

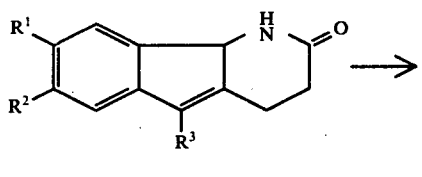

XI

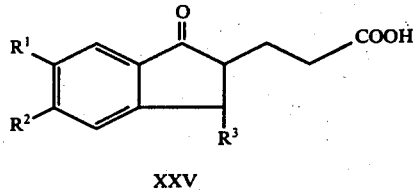

XXV

The reaction can be performed in different solvents, or mixtures of solvents, for example water, alcohols, for example methanol or ethanol, water/alcohol mixtures, in the presence of bases, such as sodium or potassium hydroxide or in the presence of acids, for example sulfuric acid or phosphoric acid. This reaction is followed by converting the indanoylpropionic acids XXVI in the usual manner into the nitriles of formula V. It is possible to start directly from the acid or to work via the corresponding amide.

The conditions of the catalytic hydrogenation used to cyclize compounds V to compounds I may vary within wide limits. The simplest way is to work under the conditions indicated for the cyclization of compounds XIV to compounds XV. The use of Raney-Nickel as a catalyst proved to be favorable, and the temperatures used are within the range of from room temperature to 80° C and the pressures between atmospheric pressure and 100 atm. If the corresponding amine $R^4$—$NH_2$ is present, the final compounds I are directly obtained.

The starting compounds VI to be used in method e) can be prepared by reducing compounds V with a complex metal hydride. For example lithium aluminum hydride in ether or tetrahydrofurane or a mixture of both is suitable for this reduction, the temperatures at which it is carried out being between 25° C and the boiling point of the solvent. Substitution of one of the two hydrogens of the amino group in VI ($R^4$ = H) can be effected for example by reductive alkylation by means of an aldehyde of formula $R^4$— CHO according to one of the usual methods (cf. Bull. Soc. 1846, 1855 (1962)).

Cyclization according to method e) is performed according to known methods. It can be carried out in the presence of a catalyst, but also without a catalyst, in an inert solvent or without such a solvent, advantageously by keeping a compound of formula VI in an inert solvent in the presence of an acidic catalyst, preferably boron trifluoride etherate or p-toluenesulfonic acid, until the end of the reaction at a temperature ranging between 0° C and the boiling point of the solvent used. Suitable solvents are preferably ethers, such as tetrahydrofurane, dimethoxy ethane, or optionally chlorinated aliphatic, cycloaliphatic or aromatic hydrocarbons, such as cyclohexane, methylene chloride, chlorobenzene or toluene. The water formed can be eliminated, preferably by means of a water separator.

If the radical $R^4$ is to be introduced subsequently into compound VII according to method f), this is advantageously achieved by deprotonizing the secondary amine with a suitable base and reacting the anion obtained, without isolation, with the alkylating agent ($R^4$— Y). As possible combinations of bases and solvents, there are mainly considered, for example, sodium hydride/dimethyl sulfoxide, sodium hydride/tetrahydrofurane or dioxane, sodium hydride/benzene or toluene, sodium amide/benzene, sodium or potassium amide/liquid ammonia, lithium diisopropyl amide in a variety of solvents, such as, for example tetrahydrofurane, dioxane, diethyl ether, benzene, toluene.

The secondary amine VII is treated with the base in a solvent until anion formation is completed. Suitable reaction temperatures are within the range of from −78° C and the boiling point of the solvent. Then, the alkylation agent $R^4$— Y is added, the reaction temperature depending on the alkylation agent and the base/solvent combination. It may vary between −78° C and the boiling point of the solution. Compounds I are obtained from compounds VII in smooth reaction.

The radical $R^4$ may be introduced into compound VII also in such a manner that, under the usual conditions (for example, pyridine, acid anhydride, room temperature), an N-acyl derivative is prepared starting from compound VII and a suitable acid derivative, and the carbonyl function is subsequently reduced in analogy to the reduction of compound II to compound I.

$R^4$ can be introduced into compounds VII also by preparing the corresponding ammonium salt XXVI from a compound VIi and an aldehyde of formula $R^5$—CO($R^4$ = $R^5$—$CH_2$—), which salt is then reduced with a complex hydride, for example $NaBH_4$ in tetrahydrofurane, to compounds I.

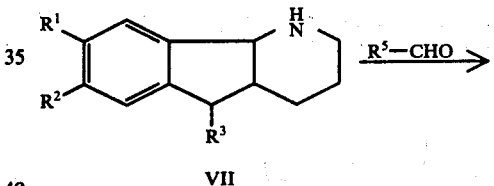

VII

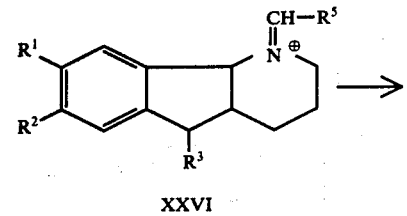

XXVI

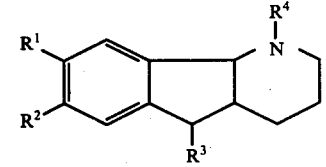

I

Conversion of VII into XXVI succeeds best when a temperature within the range of from 0° C to room temperature is chosen and the perchlorate salt of compound VII is reacted in ether with the aldehyde ($R^5$—CHO). Without isolating the perchlorate of XXVI, it is reduced as a crude product in the same solvent to compound I (cf. J. Org. Chem. 28, 3021 (1963)).

A different embodiment of the last-mentioned method is the well-known reaction with formaldehyde and formic acid which can also be used in this case to introduce a methyl group into a secondary amine to prepare compounds I ($R^4 = CH_3$) from VII (cf. Org. React. 5, 301 (1949)).

As any aromatic radical, the fused benzene ring can be subjected to an electrophilic substitution so that according to method g) generally all substituents $R^1$ and $R^2$ which allow such a substitution can be introduced in the 7- or 8-position of the indeno [1,2-b]pyridine. For this purpose, halogenation, sulfonation and especially nitration may be mentioned. In this process, compounds of formula VII are nitrated under the conditions generally used (sulfuric acid, nitric acid, ice cooling). The following working-up is especially simple if possible secondary nitrations at radical $R^3$ are excluded by blocking the corresponding position. In this way, 7- and 8-nitrohexahydroindeno[1,2-b]pyridines can be obtained. If one of the substituents $R^1$ or $R^2$ is already present, the second substituent $R^1$ or $R^2$ can also be introduced by electrophilic substitution, especially by halogenation, sulfonation or nitration. In this case, too, the nitration is especially important. It can be performed under the usual conditions, as described above.

Also the radical $R^3$, if standing for the phenyl ring, can be subjected to an electrophilic substitution, by which all those substituents to which such an electrophilic substitution is applicable can be introduced according to method h).

Also in this case, halogenation, sulfonation or nitration are the main reactions, the nitration being especially important. It is performed in the usual manner, as described in method g) and gives especially good results if potential further substitution positions, for example the 7- or 8-position, are blocked by substituents $R^1$ and $R^2$ already present and so cannot enter into a reaction.

According to method i), the substituents $R^1$, $R^2$, $R^4$ introduced subsequently or already present and those at radical $R^3$ can be modified subsequently, so that further compounds of formula I are formed. In the following, this is illustrated by several examples out of a multitude of possibilites. By reduction of an aromatic nitro group, an amine is obtaned; for example if $R^3$ stands for the 4-nitrobenzene radical, the corresponding 4-aminophenyl compound is obtained. Reduction is performed as usual, a hydrogenation advantageously being carried out with a metal catalyst, for example Raney-Nickel, optionally in a solvent, for example ethanol. A further example is the acylation of an amino group. For example, $R^3$, if it stands for the 3-aminophenyl radical, can be converted under the usual conditions, for example with acetanhydride in pyridine at lower temperatures (0°-10° C), into the 3-acetylaminophenyl radical. Likewise, an amino group can be converted into the corresponding alkylamino group by alkylation, for example with an alkyl ester of an inorganic acid, such as dimethylsulfate. In the case of dimethylsulfate, the methylamino or dimethylamino compound can be isolated. Diazotization of an aromatic amino group and subseqent reaction with a nucleophilic group is a further possibility for modifying substitutents already present. For example, a radical $R^3$, if it stands for the 3-aminophenyl group, can be converted with nitrous acid (generally prepared from sodium nitrite and sulfuric acid), into the corresponding diazonium salt at low temperatures (0°-5° C), which then yields the 3-chlorobenzene radical, for example with hydrochloric acid in the presence of copper chloride, and the 3-hydroxyphenyl group by boiling. Cleavage of an alkoxy group to the corresponding hydroxy compound is also a method for modification of substituents. For example, ether cleavage of a 7-methoxy compound ($R^2 = OCH_3$) with, for example, hydrobromide in aqueous acetic acid or with pyridine hydrochloride at a temperature within the range of from room temperature to 190° C, yields the corresponding 7-hydroxy compound.

An aromatic hydroxy compound can be converted into an alkoxy compound, for example by alkylating it with an alkyl halide in a polar solvent, such as, for example dimethyl formamide in the presence of a base, such as, for example, potassium carbonate, or by reacting it with a diazo alkane in an inert solvent (for example, diazo methane ether, room temperature).

Further examples are the oxidation of a methyl group to a carboxy group, or the conversion of a carboxy group to an amino group. For example, if the radical $R^3$ stands for the 2-methylphenyl radical, the methyl group can be oxidized by refluxing with dilute nitric acid to yield a carboxy group and, for example this carboxy group can be converted with polyphosphoric acid and hydroxyl amine at 120° to 150° C into the corresponding 2-aminophenyl-derivative.

Under the conditions used for the epimerization of the substituent $R^3$ in the 5-position of the indeno-pyridine ring (cf. page 41), a substitution or a fragmention of suitable selected substituents at the aromatic ring system is possible besides epimerisation of the substituent in the 5-position.

Under the typical reaction conditions for the eipimerization, for example a 4-n-butoxyphenyl radical is obtained, provided that $R^3$ is the 4-fluorophenyl radical. If $R^3$ is the 2-fluorophenyl radical and $R^4$ is hydrogen, the 3-n-butoxyphenyl radical is obtained from the 2-fluorophenyl radical via dehydrobenzene and the following addition of, for example n-butanol. Fragmentation under the typical epimerization conditions occurs, for example, when $R^1$ and $R^2$ are both an alkoxy group. For example, the 7,8-dimethoxy-substituted compound yields the 7-hydroxy-8-methoxy compound.

Conversion of the radical $R^4$ into another radical $R^4$ can be effected, for example, by dehalogenation or removal of a p-toluenesulfonyloxy group by means of catalytical hydrogenation or reduction with a complexed hydride. The starting compounds required therefore can be prepared according to one of the methods mentioned above. Dehalogenation can be effectd, for example, if $R^4$ is 4-chlorobutyl, catalytically with hydrogen under a pressure of 50 – 150 atm. at a temperature ranging from 40 to 120° C, whereby the radical $R^4$ is transformed into the unsubstituted butyl radical. A further possibility is the reduction of compounds I, if, for example, $R^4$ is 4-toluenesulfonyloxybutyl, with lithium aluminum hydride in ether or tetrahydrofurane under reflux to form compounds I in which $R^4$ is $C_4H_9$. Likewise, compounds I in which $R^4$ is an unsaturated radical, for example the allyl grouping, can be converted by catalytic hydrogenation under the usual conditions into compounds I which carry a saturated radical $R^4$, in this case the propyl radical.

In addition to the compounds listed in the Examples, the following compounds can be prepared by preference:

5-(2-Hydroxyphenyl)-2,3,4,4a,5,9b-hexahydro-1H-indeno[1,2-b]pyridine 5-(3-Hydroxyphenyl)-2,3,4,4a,5,9b-hexahydro-1H-indeno[1,2-b]pyridine 5-(4-Hydroxyphenyl)-2,3,4,4a,5,9b-hexahydro-1H-indeno[1,2-b]pyridine 1-Methyl-5-(4-hydroxyphenyl)-2,3,4,4a,5,9b-hexahydro-1H-indeno [1,2-b]pyridine.
1-Methyl-5-(3-hydroxyphenyl)-2,3,4,4a,5,9b-hexahydro-1H-indeno[1,2-b]pyridine.
1-Methyl-5-(2-hydroxyphenyl)-2,3,4,4a,5,9b-hexahydro-1H-indeno[1,2-b]pyridine.
1-Methyl-5-(4-aminophenyl)-2,3,4,4a,5,9b-hexahydro-1H-indeno[1,2-b]pyridine
1-Methyl-5-(3-aminophenyl)-2,3,4,4a,5,9b-hexahydro-1H-indeno[1,2-b]pyridine
1-Methyl-5-(2-aminophenyl)-2,3,4,4a,5,9-b-hexahydro-1H-indeno[1,2-b]pyridine
5-(2-Aminophenyl)-2,3,4,4a,5,9b-hexahydro-1H-indeno[1,2-b]pyridine
5-(4-Aminophenyl)-7-methoxy-2,3,4,4a,5,9b-hexahydro-1H-indeno[1,2-b]pyridine
5-(3-Aminophenyl)-7-methoxy-2,3,4,4a,5,9b-hexahydro-1H-indeno[1,2-b]pyridine
5-(2-Aminophenyl)-7-methoxy-2,3,4,4a,5,9b-hexahydro-1H-indeno[1,2-b]pyridine
5-(4-Aminophenyl)-7-hydroxy-2,3,4,4a, 5,9b-hexahydro-1H-indeno[1,2-b]pyridine
5-(3-Aminophenyl)-7-hydroxy-2,3,4,4a5,9b-hexahydro-1H-indeno[1,2-b]pyridine
5-(2-Aminophenyl)-7-hydroxy-2,3,4,4a,5,9b-hexahydro-1H-indeno[1,2-b]pyridine
5-(4-Aminophenyl)-8-methoxy-2,3,4,4a,5,9b-hexahydro-1H-indeno]1,2-b]pyridine
5-(3-Aminophenyl)-8-methoxy-2,3,4,4a,5,9b-hexahydro-1H-indeno[1,2-b]pyridine
5-(2-Aminophenyl)-8-methoxy-2,3,4,4a,5,9b-hexahydro-1H-indeno[1,2-b]pyridine
5-(4-Aminophenyl)-8-hydroxy-2,3,4,4a,5,9b-hexahydro-1H-indeno[1,2-b]pyridine
5-(3-Aminophenyl)-8-hydroxy-2,3,4,4a,5,9b-hexahydro-1H-indeno[1,2-b]pyridine
5-(2-Aminophenyl)-8-hydroxy-2,3,4,4a,5,9b-hexahydro-1H-indeno[1,2-b]pyridine
5-(4-Aminophenyl)-7-chloro-2,3,4,4a, 5,9b-hexahydro-1H-indeno[1,2-b]pyridine
5-(3-Aminophenyl)-7-chloro-2,3,4,4a,5,9b-hexahydro-1H-indeno[1,2-b]pyridine
5-(2-Aminophenyl)-7-chloro-2,3,4,4a,5,9b-hexahydro-1H-indeno[1,2-b]pyridine
5-(4-Aminophenyl)-8-chloro-2,3,4,4a,5,9b-hexahydro-1H-indeno1,2-b]pyridine
5-(3-Aminophenyl)-8-chloro-2,3,4,4a,5,9b-hexahydro-1H-indeno[1,2-b]pyridine
5-(2-Aminophenyl)-8-chloro-2,3,4,4a,5,9b-hexahydro-1H-indeno[1,2-b]pyridine
5-(4-Hydroxyphenyl)-7-chloro-2,3,4,4a,5,9b-hexahydro-1H-indeno[1,2-b]pyridine
5-(3-Hydroxyphenyl)-7-chloro-2,3,4,4a,5,9b-hexahydro-1H-indeno[1,2-b]pyridine
5-(2-Hydroxyphenyl)-7-chloro-2,3,4,4a,5,9b-hexahydro-1H-indeno[1,2-b]pyridine
5-(4-Hydroxyphenyl)-8-chloro-2,3,4,4a,5,9b-hexahydro-1H-indeno[1,2-b]pyridine
5-(3-Hydroxyphenyl)-8-chloro-2,3,4,4a,5,9b-hexahydro-1H-indeno[1,2-b]pyridine
5-(2-Hydroxyphenyl)-8-chloro-2,3,4,4a,5,9b-hexahydro-1H-indeno[1,2-b]pyridine
5-(4-Methoxyphenyl)-7-chloro-2,3,4,4a,5,9b-hexahydro-1H-indeno[1,2-b]pyridine
5-(3-Methoxyphenyl)-7-chloro-2,3,4,4a,5,9b-hexahydro-1H-inddeno[1,2-b]pyridine
5-(2-Methoxyphenyl)-7-chloro-2,3,4,4a,5,9b-hexahydro-1H-indeno[1,2-b]pyridine
5-(4-Methoxyphenyl)-8-chloro-2,3,4,4a,5,9b-hexahydro-1H-indeno[1,2-b]pyridine
5-(3-Methoxyphenyl)-8-chloro-2,3,4,4a,5,9b-hexahydro-1H-indeno[1,2-b]pyridine
5-(2-Methoxyphenyl)-8-chloro-2,3,4,4a,5,9b-hexahydro-1H-indeno[1,2-b]pyridine
5-(4-Methylphenyl)-7-chloro-2,3,4,4a,5,9b-hexahydro-1H-indeno[1,2-b]pyridine
5-(3-Methylphenyl)-7-chloro-2,3,4,4a,5,9b-hexahydro-1H-indeno[1,2-b]pyridine
5-(2-Methylphenyl)-7-chloro-2,3,4,4a,5,9b-hexahydro-1H-indeno[1,2-b]pyridine
5-(4-Methylphenyl)-8-chloro-2,3,4,4a,5,9b-hexahydro-1H-indeno[1,2-b]pyridine
5-(3-Methylphenyl)-8-chloro-2,3,4,4a,5,9b-hexahydro-1H-indeno[1,2-b]pyridine
5-(2-Methylphenyl)-8-chloro-2,3,4,4a,5,9b-hexahydro-1H-indeno[1,2-b]pyridine
5-(4-Methylphenyl)-7-methoxy-2,3,4,4a,5,9b-hexahydro-1H-indeno[1,2-b]pyridine
5-(3-Methylphenyl)-7-methoxy-2,3,4,4a,5,9b-hexahydro-1H-indeno[1,2-b]pyrridine
5-(2-Methylphenyl)-7-methoxy-2,3,4,4a,5,9b-hexahydro-1H-indeno[1,2-b]pyridine
5-(4-Methylphenyl)-8-methoxy-2,3,4,4a,5,9b-hexahydro-1H-indeno[1,2-b]pyridine
5-(3-Methylphenyl)-8-methoxy-2,3,4,4a,5,9b-hexahydro-1H-indeno[1,2-b]pyridine
5-(2-Methylphenyl)-8-methoxy-2,3,4,4a,5,9b-hexahydro-1H-indeno[1,2-b]pyridine
5-(4-Methylphenyl)-7-hydroxy-2,3,4,4a,5,9b-hexahydro-1H-indeno[1,2-b]pyridine
5-(3-Methylphenyl)-7-hydroxy-2,3,4,4a,5,9b-hexahydro-1H-indeno[1,2-b]pyridine
5-(2-Methylphenyl)-7-hydroxy-2,3,4,4a,5,9b-hexahydro-1H-indeno[1,2-b]pyridine
5-(4-Methylphenyl)-8-hydroxy-2,3,4,4a,5,9b-hexahydro-1H-indeno[1,2-b]pyridine
5-(3-Methylphenyl)-8-hydroxy-2,3,4,4a,5,9b-hexahydro-1H-indeno[1,2-b]pyridine
5-(2-Methylphenyl)-8-hydroxy-2,3,4,4a,5,9b-hexahydro-1H-indeno[1,2-b]pyridine
5-Phenyl-7-methoxy-2,3,4,4a,5,9b-hexahydro-1H-indeno[1,2-b]pyridine
5-Phenyl-8-methoxy-2,3,4,4a,5,9b-hexahydro-1H-indeno[1,2-b]pyridine
5-Phenyl-7-hydroxy-2,3,4,4a,5,9b-hexahydro-1H-indeno[1,2-b]pyridine
5-Phenyl-8-hydroxy-2,3,4,4a,5,9b-hexahydro-1H-indeno[1,2-b]pyridine
5-Phenyl-7-chloro-2,3,4,4a,5,9b-hexahydro-1H-indeno[1,2-b]pyridine
5-Phenyl-8-chloro-2,3,4,4a,5,9b-hexahydro-1H-indeno[1,2-b]pyridine
5-Thienyl-7-methoxy-2,3,4,4a,5,9b-hexahydro-1H-indeno[1,2-b]pyridine
5-Thienyl-8-methoxy-2,3,4,4a,5,9b-hexahydro-1H-indeno[1,2-b]pyridine
5-Thienyl-7-hydroxy-2,3,4,4a,5,9b-hexahydro-1H-indeno[1,2-b]pyridine
5-Thienyl-8-hydroxy-2,3,4,4a,5,9b-hexahydro-1H-indeno[1,2-b]pyrydine
5-Thienyl-7-chloro-2,3,4,4a,5,9b-hexahydro-1-H-indeno[1,2-b]pyridine
5-Thienyl-8-chloro-2,3,4,4a,5,9b-hexahydro-1H-indeno[1,2-b]pyridine
5-(2-Trifluoromethylphenyl)-7-methoxy-2,3,4,4a,5,9b-hexahydro-1H-indeno[1,2-b]pyridine 5-(3-Trifluoromethylphenyl)-7-methoxy-
2,3,4,4a,5,9b-hexahydro-1H-indeno[1,2-b]pyridine
5-(4-Trifluoromethylphenyl)-7-methoxy-
2,3,4,4a,5,9b-hexahydro-1H-indeno[1,2-b]pyridine
5-(2-Trifluoromethylphenyl)-8-methoxy-
2,3,4,4a,5,9b-hexahydro-1H-indeno[1,2-b]pyridine
5-(3-Trifluoromethylphenyl)-8-methoxy-
2,3,4,4a,5,9b-hexahydro-1H-indeno[1,2-b]pyridine
5-(4-Trifluoromethylphenyl)-8-methoxy-
2,3,4,4a,5,9b-hexahydro-1H-indeno[1,2-b]pyridine
5-(2-Trifluoromethylphenyl)-7-hydroxy-
2,3,4,4a,5,9b-hexahydro-1H-indeno[1,2-b]pyridine
5-(3-Trifluoromethylphenyl)-7-hydroxy-
2,3,4,4a,5,9b-hexahydro-1H-indeno[1,2-b]pyridine
5-(4-Trifluoromethylphenyl)-7-hydroxy-
2,3,4,4a,5,9b-hexahydro-1H-indeno[1,2-b]pyridine
5-(2-Trifluoromethylphenyl)-8-hydroxy-
2,3,4,4a,5,9b-hexahydro-1H-indeno[1,2-b]pyridine
5-(3-Trifluoromethylphenyl)-8-hydroxy-
2,3,4,4a,5,9b-hexahydro-1H-indeno[1,2-b]pyridine
5-(4-Trifluoromethylphenyl)-8-hydroxy-
2,3,4,4a,5,9b-hexahydro-1H-indeno[1,2-b]pyridine
5-(2-Trifluoromethylphenyl)-7-chloro-2,3,4,4a,5,9b-
hexahydro-1H-indeno[1,2-b]pyridine
5-(3-Trifluoromethylphenyl)-7-chloro-2,3,4,4a,5,9b-
hexahydro-1H-indeno[1,2-b]pyridine
5-(4-Trifluoromethylphenyl)-7-chloro-2,3,4,4a,5,9b-
hexahydro-1H-indeno[1,2-b]pyridine
5-(2-Trifluoromethylphenyl)-8-chloro-2,3,4,4a,5,9b-
hexahydro-1H-indeno[1,2-b]pyridine
5-(3-Trifluoromethylphenyl)-8-chloro-2,3,4,4a,5,9b-
hexahydro-1H-indeno[1,2-b]pyridine
5-(4-Trifluoromethylphenyl)-8-chloro-2,3,4,4a,5,9b-
hexahydro-1H-indeno[1,2-b]pyridine
5-(2-Chlorophenyl)-7-methoxy-2,3,4,4a,5,9b-hexahydro-1H-indeno[1,2-b]pyridine
5-(3-Chlorophenyl)-7-methoxy-2,3,4,4a,5,9b-hexahydro-1H-indeno1,2-b]pyridine
5-(4-Chlorophenyl)-7-methoxy-2,3,4,4a,5,9b-hexahydro-1H-indeno[1,2-b]pyridine
5-(2-Chlorophenyl)-8-methoxy-2,3,4,4a,5,9b-hexahydro-1H-indeno[1,2-b]pyridine
5-(3-Chlorophenyl)-8-methoxy-2,3,4,4a,5,9b-hexahydro-1H-indeno[1,2-b]pyridine
5-(4-Chlorophenyl)-8-methoxy-2,3,4,4a,5,9b-hexahydro-1H-indeno[1,2-b]pyridine
5-(2-Chlorophenyl)-7-hydroxy-2,3,4,4a,5,9b-hexahydro-1H-indeno[1,2-b]pyridine
5-(3-Chlorophenyl)-7-hydroxy-2,3,4,4a,5,9b-hexahydro-1H-indeno[1,2-b]pyridine
5-(4-Chlorophenyl)-7-hydroxy-2,3,4,4a,5,9b-hexahydro-1H-indeno[1,2-b]pyridine
5-(2-Chlorophenyl)-8-hydroxy-2,3,4,4a,5,9b-hexahydro-1H-indeno[1,2-b]pyridine
5-(3-Chlorophenyl)-8-hydroxy-2,3,4,4a,5,9b-hexahydro-1H-indeno[1,2-b]pyridine
5-(4-Chlorophenyl)-8-hydroxy-2,3,4,4a,5,9b-hexahydro-1H-indeno[1,2-b]pyridine
5-(2-Chlorophenyl)-7-chloro-2,3,4,4a,5,9b-hexahydro-1H-indeno[1,2-b]pyridine
5-(3-Chlorophenyl)-7-chloro-2,3,4,4a,5,9b-hexahydro-1H-indeno[1,2-b]pyridine
5-(4-Chlorophenyl)-7-chloro-2,3,4,4a,5,9b-hexahydro-1H-indeno[1,2-b]pyridine
5-(2-Chlorophenyl)-8-chloro-2,3,4,4a,5,9b-hexahydro-1H-indeno[1,2-b]pyridine
5-(3-Chlorophenyl)-8-chloro-2,3,4,4a,5,9b-hexahydro-1H-indeno[1,2-b]pyridine
5-(4-Chlorophenyl)-8-chloro-2,3,4,4a,5,9b-hexahydro-1H-indeno[1,2-b]pyridine
5-(2-Fluorophenyl)-7-methoxy-2,3,4,4a,5,9b-hexahydro-1H-indeno[1,2-b]pyridine
5-(3-Fluorophenyl)-7-methoxy-2,3,4,4a,5,9b-hexahydro-1H-indeno[1,2-b]pyridine
5-(4-Fluorophenyl)-7-methoxy-2,3,4,4a,5,9b-hexahydro-1H-indeno[1,2-b]pyridine
5-(2-Fluorophenyl)-8-methoxy-2,3,4,4a,5,9b-hexahydro-1H-indeno[1,2-b]pyridine
5-(3-Fluorophenyl)-8-methoxy-2,3,4,4a,5,9b-hexahydro-1H-indeno[1,2-b]pyridine
5-(4-Fluorophenyl)-8-methoxy-2,3,4,4a,5,9b-hexahydro-1H-indeno[1,2-b]pyridine
5-(2-Fluorophenyl)-7-hydroxy-2,3,4,4a,5,9b-hexahydro-1H-indeno[1,2-b]pyridine
5-(3-Fluorophenyl)-7-hydroxy-2,3,4,4a,5,9b-hexahydro-1H-indeno[1,2-b]pyridine
5-(4-Fluorophenyl)-7-hydroxy-2,3,4,4a,5,9b-hexahydro-1H-indeno[1,2-b]pyridine
5-(2-Fluorophenyl)-8-hydroxy-2,3,4,4a,5,9b-hexahydro-1H-indeno[1,2-b]pyridine
5-(3-Fluorophenyl)-8-hydroxy-2,3,4,4a,5,9b-hexahydro-1H-indeno[1,2-b]pyridine
5-(4-Fluorophenyl)-8-hydroxy-2,3,4,4a,5,9b-hexahydro-1H-indeno[1,2-b]pyridine
5-(2-Fluorophenyl)-7-chloro-2,3,4,4a,5,9b-hexahydro-1H-indeno[1,2-b]pyridine
5-(3-Fluorophenyl)-7-chloro-2,3,4,4a,5,9b-hexahydro-1H-indeno[1,2-b]pyridine
5-(4-Fluorophenyl)-7-chloro-2,3,4,4a,5,9b-hexahydro-1H-indeno[1,2-b]pyridine
5-(2-Fluorophenyl)-8-chloro-2,3,4,4a,5,9b-hexahydro-1H-indeno[1,2-b]pyridine
5-(3-Fluorophenyl)-8-chloro-2,3,4,4a,5,9b-hexahydro-1H-indeno[1,2-b]pyridine
5-(4-Fluorophenyl)-8-chloro-2,3,4,4a,5,9b-hexahydro-1H-indeno[1,2-b]pyridine
5-(2-Fluorophenyl)-6,7-dimethoxy-2,3,4,4a,5,9b-hexahydro-1H-indeno[1,2-b]pyridine
5-(3-Fluorophenyl)-6,7-dimethoxy-2,3,4,4a,5,9b-hexahydro-1H-indeno[1,2-b]pyridine
5-(4-Fluorophenyl)-6,7-dimethoxy-2,3,4,4a,5,9b-hexahydro-1H-indeno[1,2-b]pyridine
5-(2-Chlorophenyl)-6,7-dimethoxy-2,3,4,4a,5,9b-hexahydro-1H-indeno[1,2-b]pyridine
5-(3-Chlorophenyl)-6,7-dimethoxy-2,3,4,4a,5,9b-hexahydro-1H-indeno[1,2-b]pyridine
5-(2-Methylphenyl)-6,7-dimethoxy-2,3,4,4a,5,9b-hexahydro-1H-indeno[1,2-b]pyridine
5-(3-Methylphenyl)-6,7-dimethoxy-2,3,4,4a,5,9b-hexahydro-1H-indeno[1,2-b]pyridine
5-(4-Methylphenyl)-6,7-dimethoxy-2,3,4,4a,5,9b-hexahydro-1H-indeno[1,2-b]pyridine
5-(2-Trifluoromethylphenyl)-6,7-dimethoxy-
2,3,4,4a,5,9b-hexahydro-1H-indeno[1,2-b]pyridine
5-(3-Trifluoromethylphenyl)-6,7-dimethoxy-
2,3,4,4a,5,9b-hexahydro1H-indeno[1,2-b]pyridine
5-(4-Trifluoromethylphenyl)-6,7-dimethoxy-
2,3,4,4a,5,9b-hexahydro-1H-indeno[1,2-b]pyridine
5-(2-Aminophenyl)-6,7-dimethoxy-2,3,4,4a,5,9b-hexahydro-1H-indeno[1,2-b]pyridine
5-(3-Aminophenyl)-6,7-dimethoxy-2,3,4,4a,5,9b-hexahydro-1H-indeno[1,2-b]pyridine
1-Methyl-5-(4-aminophenyl)-7-methoxy-
2,3,4,4a,5,9b-hexahydro-1H-indeno[1,2-b]pyridine
1-Methyl-5-(3-aminophenyl)-7-methoxy-
2,3,4,4a,5,9b-hexahydro-1H-indeno[1,2-b]pyridine 1-Methyl-5-(2-aminophenyl)-7-methoxy-2,3,4,4a,5,9b-hexahydro-1H-indeno[1,2-b]pyridine
1-Methyl-5-(4-aminophenyl)-7-hydroxy-2,3,4,4a,5,9b-hexahydro-1H-indeno[1,2-b]pyridine
1-Methyl-5-(3-aminophenyl)-7-hydroxy-2,3,4,4a,5,9b-hexahydro-1H-indeno[1,2-b]pyridine
1-Methyl-5-(2-aminophenyl)-7-hydroxy-2,3,4,4a,5,9b-hexahydro-1H-indeno[1,2-b]pyridine
1-Methyl-5-(4-aminophenyl)-8-methoxy-2,3,4,4a,5,9b-hexahydro-1H-indeno[1,2-b]pyridine
1-Methyl-5-(3-aminophenyl)-8-methoxy-2,3,4,4a,5,9b-hexahydro-1H-indeno[1,2-b]pyridine
1-Methyl-5-(2-aminophenyl)-8-methoxy-2,3,4,4a,5,9b-hexahydro-1H-indeno[1,2-b]pyridine
1-Methyl-5-(4-aminophenyl)-8-hydroxy-2,3,4,4a,5,9b-hexahydro-1H-indeno[1,2-b]pyridine
1-Methyl-5-(3-aminophenyl)-8-hydroxy-2,3,4,4a,5,9b-hexahydro-1H-indeno[1,2-b]pyridine
1-Methyl-5-(2-aminophenyl)-8-hydroxy-2,3,4,4a,5,9b-hexahydro-1H-indeno[1,2-b]pyridine
1-Methyl-5-(4-aminophenyl)-7-chloro-2,3,4,4a,5,9b-hexahydro-1H-indeno[1,2-b]pyridine
1-Methyl-5-(3-aminophenyl)-7-chloro-2,3,4,4a,5,9b-hexahydro-1H-indeno[1,2-b]pyridine
1-Methyl-5-(2-aminophenyl)-7-chloro-2,3,4,4a,5,9b-hexahydro-1H-indeno[1,2-b]pyridine
1-Methyl-5-(4-aminophenyl)-8-chloro-2,3,4,4a,5,9b-hexahydro-1H-indeno[1,2-b]pyridine
1-Methyl-5-(3-aminophenyl)-8-chloro-2,3,4,4a,5,9b-hexahydro-1H-indeno[1,2-b]pyridine
1-Methyl-5-(2-aminophenyl)-8-chloro-2,3,4,4a,5,9b-hexahydro-1H-indeno[1,2-b]pyridine
1-Methyl-5-(4-hydroxyphenyl)-7-chloro-2,3,4,4a,5,9b-hexahydro-1H-indeno[1,2-b]pyridine
1-Methyl-5-(3-hydroxyphenyl)-7-chloro-2,3,4,4a,5,9b-hexahydro-1H-indeno[1,2-b]pyridine
1-Methyl-5-(2-hydroxyphenyl)-7-chloro-2,3,4,4a,5,9b-hexahydro-1H-indeno[1,2-b]pyridine
1-Methyl-5-(4-hydroxyphenyl)-8-chloro-2,3,4,4a,5,9b-hexahydro-1H-indeno[1,2-b]pyridine
1-Methyl-5-(3-hydroxyphenyl)-8-chloro-2,3,4,4a,5,9b-hexahydro-1H-indeno[1,2-b]pyridine
1-Methyl-5-(2-hydroxyphenyl)-8-chloro-2,3,4,4a,5,9b-hexadro-1H-indeno[1,2-b]pyridine
1-Methyl-5-(4-methoxyphenyl)-7-chloro-2,3,4,4a,5,9b-hexahydro-1H-indeno[1,2-b]pyridine
1-Methyl-5-(3-methoxyphenyl)-7-chloro-2,3,4,4a,5,9b-hexahydro-1H-indeno[1,2-b]pyridine
1-Methyl-5-(2-methoxyphenyl)-7-chloro-2,3,4,4a,5,9b-hexahydro-1H-indeno[1,2-b]pyridine
1-methyl-5-(4-methoxyphenyl)-8-chloro-2,3,4,4a,5,9b-hexahydro-1H-indeno[1,2-b]pyridine
1-Methyl-5-)3-methoxyphenyl)-8-chloro-2,3,4,4a,5,9b-hexahydro-1H-indeno[1,2-b]pyridine
1Methyl-5-(2-methoxyphenyl)-8-chloro-2,3,4,4a,5,9b-hexahydro-1H-indeno[1,2-b]pryidine
1-Methyl-5-(4-methylphenyl)-7-chloro-2,3,4,4a,5,9b-hexahydro-1H-indeno[1,2-b]pyridine
1-Methyl-5-(3-Methylphenyl)-7-chloro-2,3,4,4a,5,9b-hexahydro-1H-indeno[1,2-b]pyridine
1-Methyl-5-(2-methylphenyl)-7-chloro-2,3,4,4a,5,9b-hexahydro-1H-indeno[1,2b]pyridine
1-Methyl-5-(4-methylphenyl)-8-chloro-2,3,4,4a,5,9b-hexahydro-1H-indeno[1,2-b]pyridine
1-methyl-5-(3-methylphenyl)-8-chloro-2,3,4,4a,5,9b-hexahydro-1H-indeno[1,2-b]pyridine
1-Methyl-5-(2-methylphenyl)-8-chloro-2,3,4,4a,5,9b-hexahydro-1H-indeno[1,2-b]pyridine
1-Methyl-5-(4-methylphenyl)-7-methoxy-2,3,4,4a,5,9b-hexahydro-1H-indeno[1,2-b]pyridine
1-Methyl-5-(3-methylphenyl)-7-methoxy-2,3,4,4a,5,9b-hexahydro-1H-indeno[1,2-b]pyridine
1-Methyl-5-(2-methylphenyl)-7-methoxy-2,3,4,4a,5,9b-hexahydro-1H-indeno[1,2-b]pyridine
1-Methyl-5-(4-methylphenyl)-8-methoxy-2,3,4,4a,5,9b-hexahydro-1H-indeno[1,2-b]pyridine
1-Methyl-5-(3-methylphenyl)-8-methoxy-2,3,4,4a,5,9b-hexahydro-1H-indeno[1,2-b]pyridine
1-Methyl-5-(2-methylphenyl)-8-methoxy-2,3,4,4a,5,9b-hexahydro-1H-indeno[1,2-b]pyridine
1-Methyl-5-(4-methylphenyl)-7-hydroxy-2,3,4,4a,5,9b-hexahydro-1H-indeno[1,2-b]pyridine
1-Methyl-5-(3-methylphenyl)-7-hydroxy-2,3,4,4a,5,9b-hexahydro-1H-indeno[1,2-b]pyridine
1-Methyl-5-(2-methylphenyl)-7-hydroxy-2,3,4,4a,5,9b-hexahydro-1H-indeno[1,2-b]pyridine
1-Methyl-5-(4-methylphenyl)-8-hydroxy-2,3,4,4a,5,9b-hexahydro-1H-indeno[1,2-b]pyridine
1-Methyl-5-(3-methylphenyl)-8-hydroxy-2,3,4,4a,5,9b-hexahydro-1H-indeno[1,2-b]pyridine
1-Methyl-5-(2-methylphenyl)-8-hydroxy-2,3,4,4a,5,9b-hexahydro-1H-indeno[1,2-b]pyridine
1-Methyl-5-phenyl-7-methoxy-2,3,4,4a,5,9b-hexahydro-1H-indeno[1,2-b]pyridine
1-Methyl-5-phenyl-8-methoxy-2,3,4,4a,5,9b-hexahydro-1H-indeno[1,2-b]pyridine
1-Methyl-5-phenyl-7-hydroxy-2,3,4,4a,5,9b-hexahydro-1H-indeno[1,2-b]pyridine
1-Methyl-5-phenyl-8-hydroxy-2,3,4,4a,5,9b-hexahydro-1H-indeno [1,2-b]pyridine
1-Methyl-5-phenyl-7-chloro-2,3,4,4a,5,9b-hexahydro-1H-indeno [1,2-b]pyridine
1-Methyl-5-phenyl-8-chloro-2,3,4,4a,5,9b-hexahydro-1H-indeno [1,2-b]pyridine
1-Methyl-5-thienyl-7-methoxy-2,3,4,4a,5,9b-hexahydro-1H-indeno [1,2-b]pyridine
1-Methyl-5-theinyl-8-methoxy-2,3,4,4a,5,9b-hexahydro-1H-indeno [1,2-b]pyridine
1-Methyl-5-thienyl-7-hydroxy-2,3,4,4a,5,9b-hexahydro-1H-indeno [1,2-b]pyridine
1-Methyl-5-thienyl-8-hydroxy-2,3,4,4a,5,9b-hexahydro-1H-indeno [1,2-b]pyridine
1-Methyl-5-thienyl-7-chloro-2,3,4,4a,5,9b-hexahydro-1H-indeno [1,2-b]pyridine
1-Methyl-5-thienyl-8-chloro-2,3,4,4a,5,9b-hexahydro-1H-indeno [1,2-b]pyridine
1-Methyl-5-(2-trifluoromethylphenyl)-7-methoxy-2,3,4,4a,5,9b-hexahydro-1H-indeno[1,2-b]pyridine
1-Methyl-5-(3-trifluoromethylphenyl)-7-methoxy-2,3,4,4a,5,9b-hexahydro-1H-jindeno[1,2-b]pyridine
1-Methyl-5-(4-trifluoromethylphenyl)-7-methoxy-2,3,4,4a,5,9b-hexahydro-1H-indeno[1,2-b]pyridine
1-Methyl-5-(2-trifluoromethylphenyl)-8-methyoxy-2,3,4,4a,5,9b-hexahydro-1H-indeno[1,2-b]pyridine
1-Methyl-5-(3-trifluoromethylphenyl)-8-methoxy-2,3,4,4a,5,9b-hexahydro-1H-indeno[1,2-b]pyridine
1-Methyl-5-(4-trifluoromethylphenyl)-8-methoxy-2,3,4,4a,5,9b-hexahydro-1H-indeno[1,2-b]pyridine
1-Methyl-5-(2-trifluoromethylphenyl)-7-hydroxy-2,3,4,4a,5,9b-hexahydro-1H-indeno[1,2-b]pyridine
1-Methyl-5-(3-trifluoromethylphenyl)-7-hydroxy-2,3,4,4a,5,9b-hexahydro-1H-indeno[1,2-b]pyridine
1-Methyl-5-(4-trifluoromethylphenyl)-7-hydroxy-2,3,4,4a,5,9b-hexahydro-1H-indeno[1,2-b]pyridine
1-Methyl-5-(2-trifluoromethylphenyl)-8-hydroxy-2,3,4,4a,5,9b-hexahydro-1H-indeno[1,2-b]pyridine 1-Methyl-5-(3-trifluoromethylphenyl)-8-hydroxy-2,3,4,4a,5,9b-hexahydro-1H-indeno[1,2-b]pyridine
1-Methyl-5-(4-trifluoromethylphenyl)-8-hydroxy-2,3,4,4a,5,9b-hexahydro-1H-indeno[1,2-b]pyridine
1-Methyl-5-(2-trifluoromethylphenyl)-7-chloro-2,3,4,4a,5,9b-hexahydro-1H-indeno[1,2-b]pyridine
1-Methyl-5-(3-trifuloromethylphenyl)-7-chloro-2,3,4,4a,5,9b-hexahydro-1H-indeno[1,2-b]pyridine
1-Methyl-5-(4-trifluoromethylphenyl)-7-chloro-2,3,4,4a,5,9b-hexahydro-1H-indeno[1,2-b]pyridine
1-Methyl-5-(2-trifluoromethylphenyl)-8-chloro-2,3,4,4a,5,9b-hexahydro-1H-indeno[1,2-b]pyridine
1-Methyl-5-(3-trifluoromethylphenyl)-8-chloro-2,3,4,4a,5,9b-hexahydro-1H-indeno[1,2-b]pyridine
1-Methyl-5-(4-trifluoromethylphenyl)-8-chloro-2,3,4,4a,5,9-hexahydro-1H-indeno[1,2-b]pyridine
1-Methyl-5-(2-chlorophenyl)-7-methoxy-2,3,4,4a,5,9b-hexahydro-1H-indeno[1,2-b]pyridine
1-Methyl-5-(3-chlorophenyl)-7-methoxy-2,3,4,4a,5,9b-hexahydro-1H-indeno[1,2-b]pyridine
1-Methyl-5-(4-chlorophenyl)-7-methoxy-2,3,4,4a,5,9b-hexahydro-1H-indeno[1,2-b]pyridine
1-Methyl-5-(2-chlorophenyl)-8-methoxy-2,3,4,4a,5,9b-hexahydro-1Hl-indeno[1,2-b]pyridine
1-Methyl-5-(3-chlorophenyl)-8-methoxy-2,3,4,4a,5,9b-hexahydro-1H-indeno[1,2-b]pyridine
1-Methyl-5-(4-chlorophenyl)-8-methoxy-2,3,4,4a,5,9b-hexahydro-1H-indeno[1,2-b]pyridine
1-Methyl-5-(2-chlorophenyl)-7-hydroxy-2,3,4,4a,5,9b-hexahydro-1H-indeno[1,2-b]pyridine
1-Methyl-5-(3-chlorophenyl)-7-hydroxy-2,3,4,4a,5,9b-hexahydro-1H-indeno[1,2-b]pyridine
1-Methyl-5-(4-chlorophenyl)-7-hydroxy-2,3,4,4a,5,9b-hexahydro-1H-indeno[1,2-b]pyridinne
1-Methyl-5-(2-chlorophenyl)-8-hydroxy-2,3,4,4a,5,9b-hexahydro-1H-indeno[1,2-b]pyridine
1-Methyl-5-(3-chlorophenyl)-8-hydroxy-2,3,4,4a,5,9b-hexahydro-1H-indeno[1,2-b]pyridine
1-Methyl-5-(4-chlorophenyl)-8-hydroxy-2,3,4,4a,5,9b-hexahydro-1H-indeno[1,2-b]pyridine
1-Methyl-5-(2-chlorophenyl)-7-chloro-2,3,4,4a,5,9b-hexahydro-1H-indeno[1,2-b]pyridine
1-Methyl-5-(3-chlorophenyl)-7-chloro-2,3,4,4a,5,9b-hexahydro-1H-indeno[1,2-b]pyridine
1-Methyl-5-(4-chlorophenyl)-7-chloro-2,3,4,4a,5,9b-hexahydro-1H-indeno[1,2-b]pyridine
1-Methyl-5-(2-chlorophenyl)-8-chloro-2,3,4,4a,5,9b-hexahydro-1H-indeno[1,2-b]pyridine
1-Methyl-5-(3-chlorophenyl)-8-chloro-2,3,4,4a,5,9b-hexahydro-1H-indeno[1,2-b]pyridine
1-Methyl-5-(4-chlorophenyl)-[-chloro-2,3,4,4a,5,9b-hexahydro-1H-indeno[1,2-b]pyridine
1-Methyl-5-(2-fluorophenyl)-7-methoxy-2,,3,4,4a,5,9b-hexahydro-1H-indeno[1,2-b]pyridine
1-Methyl-5-(3-fluorophenyl)-7-methoxy-2,3,4,4a,5,9b-hexahydro-1H-indeno[1,2-b]pyridine
1-Methyl-5-(4-fluorophenyl)-7-methoxy-2,3,4,4a,5,9b-hexahydro-1H-indeno[1,2-b]pyridine
1-Methyl-5-(2-fluorophenyl)-8-methoxy-2,3,4,4a,5,9b-hexahydro-1H-indeno[1,2-b]pyridine
1-Methyl-5-(3-fluorophenyl)-8-methoxy-2,3,4,4a,5,9b-hexahydro-1H-indeno[1,2-b]pyridine
1-Methyl-5-(4-fluorophenyl)-8-methoxy-2,3,4,4a,5,9b-hexahydro-1H-indeno[1,2-b]pyridine
1-Methyl-5-(2-fluorophenyl)-7-hydroxy-2,3,4,4a,5,9b-hexahydro-1H-indeno[1,2-b]pyridine
1-Methyl-5-(3-fluorophenyl)-7-hydroxy-2,3,4,4a,5,9b-hexahydro-1H-indeno[1,2-b]pyridine
1-Methyl-5-(4-fluorophenyl)-7-hydroxy-2,3,4,4a,5,9b-hexahydro-1H-indeno[1,2-b]pyridine
1-Methyl-5-(2-fluorophenyl)-8-hydroxy-2,3,4,4a,5,9b-hexahydro-1H-indeno[1,2-b]pyridine
1-Methyl-5-(3-fluorophenyl)-8-hydroxy-2,3,4,4a,5,9b-hexahydro-1H-indeno[1,2-b]pyridine
1-Methyl-5-(4-fluorophenyl)-8-hydroxy-2,3,4,4a,5,9b-hexahydro-1H-indeno[1,2-b]pyridine
1-Methyl-5-(2-fluorophenyl)-7-chloro-2,3,4,4a,5,9b-hexahydro-1H-indeno[1,2-b]pyridine
1-Methyl-5-(3-fluorophenyl)-7-chloro-2,3,4,4a,5,9b-hexahydro-1H-indeno[1,2-b]pyridine
1-Methyl-5-(4-fluorophenyl)-7-chloro-2,3,4,4a,5,9b-hexahydro-1H-indeno[1,2-b]pyridine
1-Methyl-5-(2-fluorophenyl)-8-chloro-2,3,4,4a,5,9b-hexahydro-1H-indeno[1,2-b]pyridine
1-Methyl-5-(3-fluorophenyl)-8-chlor-2,3,4,4a,5,9b-hexahydro-1H-indeno[1,2-b]pyridine
1-Methyl-5-(4-fluorophenyl)-8-chlor-2,3,4,4a,5,9b-hexahydro-1H-indeno[1,2-b]pyridine
1-Methyl-5-(2-fluorophenyl)-6,7-dimethoxy-2,3,4,4a,5,9b-hexahydro-1H-indeno[1,2-b]pyridine
1-Methyl-5-(3-fluorophenyl)-6,7-dimethoxy-2,3,4,4a,5,9b-hexahydro-1H-indeno[1,2-b]pyridine
1-Methyl-5-(4-fluorophenyl)-6,7-dimethoxy-2,3,4,4a,5,9b-hexahydro-1H-indeno[1,2-b]pyridine
1-Methyl-5-(2-chlorophenyl)-6,7-dimethoxy-2,3,4,4a,5,9b-hexahydro-1H-indeno[1,2-b]pyridine
1-Methyl-5-(3-chlorophenyl)-6,7-dimethoxy-2,3,4,4a,5,9b-hexahydro-1H-indeno[1,2-b]pyridine
1-Methyl-5-(4-chlorophenyl)-6,7-dimethoxy-2,3,4,4a,5,9b-hexahydro-1H-indeno[1,2-b]pyridine
1-Methyl-5-(2-methylhenyl)-6,7-dimethoxy-2,3,4,4a,5,9b-hexahydro-1H-indeno[1,2-b]pyridine
1-Methyl-5-(3-methylphenyl)-6,7-dimethoxy-2,3,4,4a,5,9b-hexahydro-1H-indeno[1,2-b]pyridine
1-Methyl-5-(4-methylphenyl)-6,7-dimethoxy-2,3,4,4a,5,9b-hexahydro-1H-indeno[1,2-b]pyridine
1-Methyl-5-(2-trifluoromethylphenyl)-6,7-dimethoxy-2,3,4,4a,5,9b-hexahydro-1H-indeno[1,2-b]pyridine
1-Methyl-5-(3-trifluoromethylphenyl)-6,7-dimethoxy-2,3,4,4a,5,9b-hexahydro-1H-indeno[1,2-b]pyridine
1-Methyl-5-(4-trifluoromethylphenyl)-6,7-dimethoxy-2,3,4,4a,5,9b-hexahydro-1H-indeno[1,2-b]pyridine
1-Methyl-5-(2-aminophenyl)-6,7-dimethoxy-2,3,4,4a,5,9b-hexahydro-1H-indeno[1,2-b]pyridine
1-Methyl-5-(3-aminophenyl)-6,7-dimethoxy-2,3,4,4a,5,9b-hexahydro-1H-indeno[1,2-b]pyridine
1-Methyl-5-(4-aminophenyl)-6,7-dimethoxy-2,3,4,,4a,5,9b-hexahydro-1H-indeno[1,2-b]pyridine The compounds of formula I have three asymmetrical carbon atoms, which means that in the preparation of the compounds of the invention according to the method described under b), 8 steroisomeric compounds are obtained. The invention therefore comprises all compounds of formula I irrespective of the steric arrangement at the 4a-, 5- or 9b-carbon atom. Pure racemates in which the arrangement of the substituents on the carbon atoms in 4a-, 5- and 9b-position to each other are uniform can be obtained from the isomer mixture, for example by fractional crystallization or also by column or preparative thin-layer chromatography, wherefrom the optically pure compounds can be obtained according to the usual methods, for example by treatment with optically active acids, for example L-tartaric acid.

According to method a), sterically uniform all-cis-compounds are obtained, since upon hydrogenation of compound XI to compound XII, the $H_{4a}$, $H_5$-cis-, $H_{4a}$, $H_{9b}$-cis-compounds of formula XII are obtained quantitatively and the steric centers on the 4a-, 5-and 9b-carbon atoms are not affected by the following operations, so that uniform $H_{4a}$-, $H_5$-cis-, $H_{4a}$, $H_{9b}$-cis-compounds of formula I are obtained. Sterically uniform compounds of formula I having a $H_{4a}$, $H_5$-trans, $H_{4a}$, $H_{9b}$-cis-arrangement can also be synthesized, which can be effected in such a way that compounds XII or XIII having a $H_{4a}H_5$-cis-, $H_{4a}H_{9b}$-cis-configuration are treated in an alkaline medium, for example with KOH in n-butanol. From this process the amino acids XXVII are obtained which are again cyclized by the usual methods to the lactams XII having a $H_{4a}$, $H_5$-trans-, $H_{4a}$, $H_{9b}$-cis-configuration. The following chemical reactions do not affect the stereochemistry at the carbon atoms 4a, 5 and 9b, so that uniform compounds of formula I having a $H_{4a}H_5$-trans-, $H_{4a}H_{9b}$-cis-configuration are obtained.

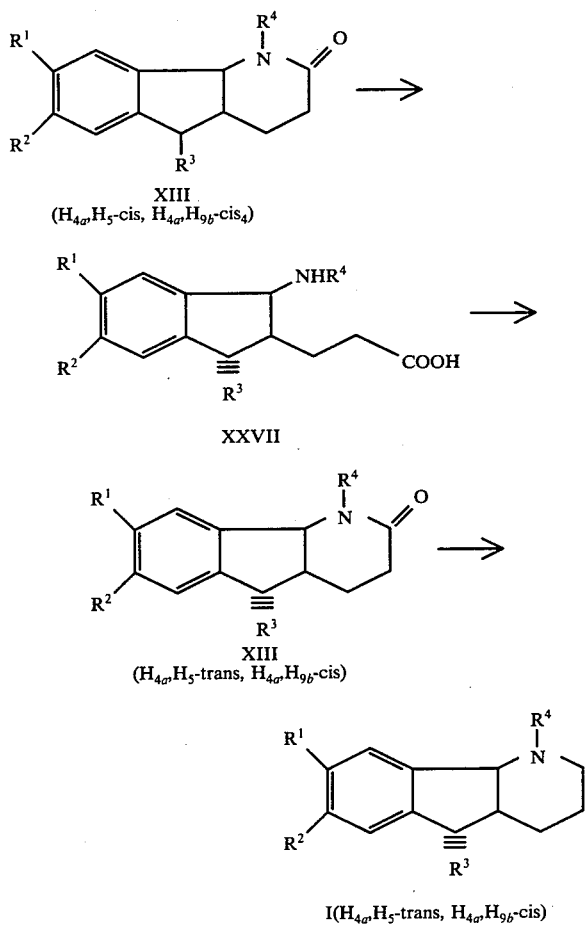

Compounds having the same steric arrangement are also obtained when the sterically uniform compounds of formula I having a $H_{4a}$, $H_5$-cis-, $H_{4a}$,$H_{9b}$-cis-configuration, which are prepared according to method a), are isomerized under thermodynamic control. For this purpose, a strong base, for example alcoholates, alkali metal hydroxides or tertiary amines, in a protic solvent, such as water or alcohols, can be used, treatment with potassium hydroxide in n-butanol at a temperature within the range of from 60° to 150° C being advantageous.

The conversion of the free amines into the physiologically acceptable salts is effected according to known methods. Suitable salts are, for example, the hydrochloride, sulfate, phosphate, lactate and citrate.

The compounds of the invention have antidepressive activity and can be used, for example, as medicaments for the treatment of psychic diseases, for example in the form of their aqueous solutions or suspensions or also as solutions in pharmacologically acceptable organic solvents, for example, mono- or polyvalent alcohols, dimethylsulfoxide or dimethylformamide, or also in the presence of pharmacologically acceptable polymer carriers, such as, for example, polyvinyl pyrrolidone. Suitable preparations are the usual galenic infusion solutions or injections solutions, preferably for administration via the intravenous and intraperitoneal route, and preparations for oral administration, such as tablets, dragees or gelatine capsules, and suppositories. For all these preparations, the usual pharmaceutical carriers may be used, such as, for example, starch, lactose, tragacanth and magnesium carbonate with the addition of other suitable materials, such as, for example, magnesium stearate. As the daily dose for a patient, approximately 0.5 mg to 300 mg, preferably 1 to 100 mg, are considered.

A dosage unit contains from 0.5 to 100 mg, preferably 1 mg to 30 mg, of a compound of the invention.

Test systems which may serve for the determination of the psychotropic effect, are, for example, the "reserpinehypothermy" test and the "tetrabenzineptosis" test on mice or rats and the electroencephalogram on cats and rabbits.

EXAMPLE 1

4a(S,R);5(S,R); 9b(S,R)
1-methyl-5-phenyl-2,3,,4,4a,5,9b-hexahydro-1H-indeno[1,2-b]pyridine-2-one 10 mmols of 4a(S,R); 5(S,R); 9b(S,R)-5-phenyl-2,3,4,4a,5,9b-hexahydro-1H-indeno[1,2b]pyridine-2-one were first placed in toluene, 25 mmols of sodium amide were added and the mixture was refluxed for 2.5 hours. After cooling to 40° C, 25 mmols of methyl iodide, dissolved in 10 ml of toluene, were added dropwise and the solution was maintained at 50° C for 1 hour, heated to 80° C and maintained at that temperature for 1 hour then refluxed for 1.5 hours. After cooling, the excess sodium amide was decomposed with water, the organic phase was washed with water several times, dried and concentrated. A pale oil was obtained which crystallized soon.

Melting point: 156° – 158° C

In an analogous manner, there were obtained the following N-alkyl-hexahydro-1H-indene[1,2-b]pyridine-2-ones:

4a(S,R); 5(S,R); 9b(S,R) 1-methyl-5-(4-methylphenyl)-2,3,4,4a, 5,9b-hexahydro-1H-indeno[1,2-b]pyridine-2-one;
melting point: 128°–130° C 4a(S,R); 5(S,R); 9b(S,R) 1-methyl-5-(4-chlorophenyl)-2,3,4,4a, 5,9b-hexahydro-1H-indeno[1,2-b]pyridine-2-one,
melting point: 196° – 198° C 4a(S,R); 5(S,R); 9b(S,R) 1-methyl-5-phenyl-6,7-dimethoxy-2,3,4,4a,5,9b-hexahydro-1H-indeno[1,2-b]pyridine-2-one, melting point: 188° – 190° C 4a(S,R); 5(S,R); 9b(S,R) 1-methyl-5-(3-methylphenyl)-2,3,4a,5 9b-hexahydro-indeno[1,2-b]pyridine-2-one,
melting point: 107° – 110° C 4a(S,R); 5(S,R); 9b(S,R) 1-methyl-5-(2-methylphenyl)-2,3,4,4a, 9b-hexahydro-indeno[1,2-b]pyridine 2-one,
melting point: 149° – 150° C 4a(S,R); 5(S,R); 9b(S,R) 1-methyl-7-methoxy-5-(4-methylphenyl)-2,3,4,4a,5,9b-hexahydro-indeno[1,2-b]pyridine-2-one, melting point: 154° – 156° C, (b) 4a(S,R); 5(S,R); 9b(S,R) 1-methyl-5-phenyl-2,3,4,4a,5,9b-hexahydro-1H-indeno[1,2-b]pyridine, 0.0325 mol of 4a(S,R); 5(S,R); 9b(S,R) 1-methyl-5-phenyl-2,3,4,4a,5,9b-hexahydro-1H-indeno[1,2-b]pyridine-2-one was suspended in 100 ml of ether and added to a solution of 0.05 mol of lithium aluminum hydride in 100 ml of ether. The mixture was refluxed for 6 hours and after cooling the excess hydride was decomposed with ethyl acetate. Water and 2 N sodium hydroxide solution were added to that solution, which was stirred for half an hour and suction-filtered. After adding ether, the organic phase was washed several times with water, dried and concentrated.
Melting point: 249° – 257° C (HCl)

In an analogous manner and on the basis of the lactames the following compounds were obtained:

EXAMPLE 2

4a(S,R); 5(S,R); 9b(S,R) 1-methyl-5-(4-methylphenyl)-2,3,4,4a,5,9b-hexahydro-1H-indeno[1,2-b]pyridine
Melting point: 244° – 246° C (HCl)

EXAMPLE 3

4a(S,R); 5(S,R); 9b(S,R) 1-methyl-5-(4-chlorophenyl)-2,3,4,4a,5,9b-hexahydro-1H-indeno[1,2-b]pyridine
Melting point: 274° – 275° C (HCl)

EXAMPLE 4

4a(S,R); 5(S,R); 9b(S,R)-5-(4-aminophenyl)-2,3,4,4a,5,9b-hexahydro-1H-indeno[1,2-b]pyridine
Melting point: 294° – 297° C (HCl)

EXAMPLE 5

4a(S,R); 5(S,R); 9b(S,R) 5-(4-chlorophenyl)-6,7-dimethoxy-2,3,4,4a,5,9b-hexahydro-1H-indeno[1,2-b]pyridine
Melting point: 263° – 266° C (HCl)

EXAMPLE 6

4a(S,R); 5(S,R); 9b(S,R) 5-(4-aminophenyl)-6,7-dimethoxy-2,3,4,4a,5,9b-hexahydro-1H-indeno[1,2-b]pyridine
Melting point: 237° – 240° C (2HCl)

EXAMPLE 7

4a(S,R); 5(S,R); 9b(S,R) 5-(3-aminophenyl)-2,3,4,4a,5,9b-hexahydro-1H-indeno[1,2-b]pyridine
Melting point: 305° – 308° C (2 HCl)

EXAMPLE 8

4a(S,R); 5(S,R); 9b(S,R) 1-methyl-5-phenyl-6,7-dimethoxy-2,3,4,4a,5,9b-hexahydro-1H-indeno[1,2-b]pyridine
Melting point: 268° – 270° C (2 HCl)

EXAMPLE 9

4a(S,R); 5(S,R); 9b(S,R) 5-(2-trifluoromethylphenyl)-2,3,4,4a,5,9b-hexahydro-1H-indeno[1,2-b]pyridine
Melting point: 226° – 230° C (HCl)

EXAMPLE 10

4a(S,R); 5(S,R); 9b(S,R) 5-phenyl-6,7-dimethoxy-2,3,4,4a,5,9b-hexahydro-1H-indeno[1,2-b]pyridine
Melting point: 234° – 236° C (HCl)

EXAMPLE 11

4a(S,R); 5(S,R); 9b(S,R) 5-(3-pyridyl)-6,7-dimethoxy-2,3,4,4a,5,9b-hexahydro-1H-indeno[1,2-b]pyridine
Melting point: 263° – 265° C (HCl)

EXAMPLE 12

4a(S,R); 5(S,R); 9b(S,R) 5-thienyl-2,3,4,4a,5,9b-hexahydro-1H-indeno[1,2-b]pyridine
Melting point: 201° – 203° C (HCl)

EXAMPLE 13

4a(S,R); 5(S,R); 9b(S,R) 5-(4-amino-3-chlorophenyl)-2,3,4,4a,5,9b-hexahydro-1H-indeno[1,2-b]pyridine
Melting point: 227° – 229° C (2 HCl)

EXAMPLE 14

4a(S,R); 5(S,R); 9b(S,R) 1-methyl-5-phenyl-2,3,4,4a,5,9b-hexahydro-1H-indeno[1,2-b]pyridine 0.05 mol of the amine prepared under 1 b) was boiled under reflux together with 150 ml of n-butanol and 150 g of potassium hydroxide for 10 hours. After cooling, the reaction mixture was shaken with a mixture of water and ether, the ether phase washed several times with water, dried and concentrated.
Melting point: 254° – 255° C (HCl)

As described in Example 14, the following stereoisomers have been prepared from the corresponding hexahydro-1H-indeno[1,2-b]pyridines:

EXAMPLE 15

4a(S,R); 5(S,R); 9b(S,R) 1-methyl-5-(4-methylphenyl)-2,3,4,4a,5,9b-hexahydro-1H-indeno[1,2-b]pyridine
Melting point: 250° – 252° C (HCl)

EXAMPLE 16

4a(S,R); 5(S,R); 9b(S,R) 1-methyl-5-(4-chlorophenyl)-2,3,4,4a,5,9b-hexahydro-1H-indeno[1,2-b]pyridine
amorphous, NMR-spectrum (τ): N-CH$_3$:2,2(s); CH—N:3,1 (d,J=5 Hz) CH—C: 4,4 (d,J=11 Hz)

EXAMPLE 17

4a(S,R); 5(S,R); 9b(S,R) 5-(4-aminophenyl)-2,3,4,4a,5,9b-hexahydro-1H-indeno[1,2-b]pyridine
Melting point: 325° – 328° C (2 HCl)

EXAMPLE 18

4a(S,R); 5(R,S); 9b(S,R) 5-(3-aminophenyl)-2,3,4-a,5,9b-hexahydro-1H-indeno[1,2-b]pyridine
Melting point: 262° – 265° C (2 HCl)

EXAMPLE 19

4a(S,R); 5(R,S); 9b(S,R) 1-methyl-5-phenyl-7-methoxy-8-hydroxy-2,3,4,4a,5,9b-hexahydro-1H-indeno[1,2-b]pyridine Melting point: 254° – 257° C (HCl)

EXAMPLE 20

4a(S,R); 5(S,R); 9b(S,R) 5-(3-methylphenyl)-2,3,4,4a,5,9b-hexahydro-1H-indeno[1,2-b]pyridine;
Melting point: 135° – 138° C

EXAMPLE 21

4a(S,R); 5(S,R); 9b(S,R) 5-(2-methylphenyl)-2,3,4,4a,5,9b-hexahydro-1H-indeno[1,2-b]pyridine;
Melting point: 199° – 202° C (HCl)

EXAMPLE 22

4a(S,R); 5(S,R); 9b(S,R) 5-(4-methylphenyl)-2,3,4,4a,5,9b-hexahydro-1H-indeno[1,2-b]pyridine;
Melting point: 296° – 299° C;

EXAMPLE 23

4a(S,R); 5(S,R); 9b(S,R) 1-methyl-5-(3-methylphenyl)-2,3,4,4a,5,9b-hexahydro-1H-indeno[1,2-b]pyridine;
Melting point: 237° – 240° C (HCl)

EXAMPLE 24

4a(S,R); 5(S,R); 9b(S,R) 1-methyl-5-(2-methylphenyl)-2,3,4,4a,5,9b-hexahydro-1H-indeno[1,2-b]pyridine;
Melting point: 263° – 265° C (HCl)

EXAMPLE 25

4a(S,R); 5(S,R); 9b(S,R); 5-(4-aminophenyl)-7-methoxy-2,3,4,4a,5,9b-hexahydro-1H-indeno[1,2-b]pyridine;
Melting point: 244° – 246° C (2 HCl)

EXAMPLE 26

4a(S,R); 5(S,R); 9b(S,R) 5-(4-aminophenyl)-7-chloro-2,3,4,4a,9b-hexahydro-1H-indeno[1,2-b]pyridine;
Melting point: 257° – 260° C (2 HCl)

EXAMPLE 27

4a(S,R); 5(S,R); 9b(S,R) 5-(4-methylphenyl)-7-methoxy-2,3,4,4a,5,9b-hexahydro-1H-indeno[1,2-b]pyridine;
Melting point: 204° – 205° C (HCl)

EXAMPLE 28

4a(S,R); 5(S,R); 9b(S,R) 1-methyl-5-(4-methylphenyl)-7-methoxy-2,3,4,4a,5,9b-hexahydro[1,2-b]pyridine;
Melting point: 115° – 120° C (HCl)

EXAMPLE 29

4a(S,R); 5(S,R); 9b(S,R) 5-(2-fluorophenyl)-2,3,4,4a,5,9b-hexahydro-1H-indeno[1,2-b]pyridine;
Melting point: 269° – 272° C (HCl)

EXAMPLE 30

4a(S,R); 5(S,R); 9b(S,R) 5-(4-fluorophenyl)-2,3,4,4a,5,9b-hexahydro-1H-indeno[1,2-b]pyridine;
Melting point: 274° – 277° C (HCl)

EXAMPLE 31

4a(S,R); 5(R,S); 9b(S,R) 1-methyl-5-(2-fluorophenyl)-2,3,4,4a,5,9b-hexahydro-1H-indeno[1,2-b]pyridine
50 mmols of 4a(S,R); 5(R,S); 9b(S,R) 5-(2-fluorophenyl)-2,3,4,4a,5,9b-hexahydro-1H-indeno[1,2-b]pyridine were dissolved while cooling in 7.5 ml of 90% formic acid to which 6.5 ml of 35% formaldehyde solution were added. After 8 hours' reflux (bath temperature: 110° C), 7 ml of concentrated HCl were added and the reaction mixture was evaporated under reduced pressure. The residue was dissolved in ether and dilute NaOH (the aqueous phase must be alkaline). The ether phase was diluted, after drying, with 10% of its volume of ethyl acetate and the hydrochloride was precipitated with methanolic HCl.
Melting point: 252° – 253° C (HCl).

EXAMPLE 32

4a(S,R); 5(S,R); 9b(S,R) 1-methyl-5-(4-fluorophenyl)-2,3,4,4a,5,9b-hexahydro-1H-indeno[1,2-b]pyridine
This compound was prepared in analogy to the prescription given in Example 31 from the compound prepared in Example 30.
Melting point: 241° – 244° C (HCl)

EXAMPLE 33

4a(S,R); 5(S,R); 9b(S,R)
5-(4-aminophenyl)-7-hydroxy-2,3,4,4a,5,9b-hexahydro-1H-indeno[1,2-b]pyridine 0.03 mol of 4a(S,R); 5(S,R); 9b(S,R) 5-(4-aminophenyl)-7-methoxy-2,3,4,4a,5,9b-hexahydro-1H-indeno[1,2-b]pyridine was dissolved in 200 ml of pyridine and dry gaseous hydrogen chloride was passed over the reaction mixture while stirring thoroughly. The mixture was heated to 160° C. During the following 3 hours, further dry gaseous hydrogen chloride was passed over the mixture at 180° C. 400 ml of water were added at room temperature, the alkaline pH was adjusted with solid potash, the mixture was extracted several times with ethyl acetate, dried and concentrated.
Melting point: 244° – 248° C (decomposition) (HCl)

In analogy to the prescription given in Example 33, the following two compounds were prepared from the corresponding methoxy compounds:

EXAMPLE 34

4a(S,R); 5(S,R); 9b(S,R) 5-(4-methylphenyl)-7-hydroxy-2,3,4,4a,5,9b-hexahydro-1H-indeno[1,2-b]pyridine.
Melting point: 249° – 251° C (HCl).

EXAMPLE 35

4a(S,R); 5(S,R); 9b(S,R) 1-methyl-5-(4-methylphenyl)-7-hydroxy-2,3,4,4a,5,9b-hexahydro-1H-indeno[1,2-b]pyridine.
Melting point: 240° – 242° C (HCl).

EXAMPLE 36

3-[3-(4-nitrophenyl)-indane-1-one-2-yl]-propionic acid 0.1 mol of 5-nitrophenyl-2,3,4,9b-tetrahydro-1H-indeno[1,2-b]pyridine-2-one was added to 500 ml of semi-concentrated hydrochloric acid and boiled under reflux for 3 hours. After cooling, the mixture was decanted and the remaining oil was dissolved in sodium bicarbonate solution. The solution was clarified with animal charcoal, acidified and the precipitated acid was introduced into methylene with shaking. After drying and concentrating, a pale uniform oil was obtained that could be used for the next reaction step without purification.

4a(S,R); 5(S,R); 9b(S,R)
1-methyl-5-(4-aminophenyl)-2,3,4,4a,5,9b-hexahydro-1H-indeno[1,2-b]pyridine-2-one 0.09 mol of 3-[3-(4-nitrophenyl)-indane-1-one-2-yl]-propionic acid was dissolved in 300 ml of 14% methanolic methylamine solution and allowed to stand overnight at room temperature under a nitrogen atmosphere. The solution was hydrogenated with Raney-Nickel during 2 hours at 50° C and under a pressure of 50 at. gage, and then again during 18 hours at 110° C under a pressure of 150 at. gage. The catalyst was filtered off and concentrated.
Melting point: 199° - 202° C.

4a(S,R); 5(S,R); 9b(S,R)
1-methyl-5-(4-aminophenyl)-2,3,4,4a,5,9b-hexahydro-1H-indeno[1,2-b]pyridine The compound was prepared in analogy to Example 1b on the basis of indeno[1,2-b]pyridine-2one.

| NMR spectrum: | N—CH$_3$ | $\Delta$ = 2.35 (s) | |
|---|---|---|---|
| | CH—C | $\Delta$ = 4.4 (d) | J = 11 Hz |
| | CH—N | $\Delta$ = 3.2 (d) | J = 5 Hz |

As described in Example 14 the following stereoisomers were prepared on the basis of the hexahydro-1H-indeno[1,2-b]pyridine;

EXAMPLE 37

4a(S,R); 5(S,R); 9b(S,R) 5-(3-methylphenyl)-2,3,4,4a,5,9b-hexahydro-1H-indeno[1,2-b]pyridine.
Melting point: 228° - 230° C (HCl)

EXAMPLE 38

4a(S,R); 5(R,S); 9b(S,R) 5-(2-methylphenyl)-2,3,4,4a,5,9b-hexahydro-1H-indeno[1,2-b]pyridine.
Melting point: 245° - 247° C (HCl)

EXAMPLE 39

4a(S,R); 5(R,S); 9b(S,R); 5-(4-methylphenyl)-2,3,4,4a,5,9b-hexahydro-1H-indeno[1,2-b]pyridine.
Melting point: 247° - 253° C (HCl)

EXAMPLE 40

4a(S,R); 5(R,S) 9b(S,R) 1-methyl-5-(3-methylphenyl)-2,3,4,4a,5,9b-hexahydro-1H-indeno[1,2-b]pyridine.
Melting point: 211° - 214° C (HCl)

EXAMPLE 41

4a(S,R); 5(R,S); 9b(S,R) 1-methyl-5(2-methylphenyl)-2,3,4,4a,5,9b-hexahydro-1H-indeno[1,2-b]pyridine.
Melting point: 248° - 249° C) (HCl)

EXAMPLE 42

4a(S,R); 5(R,S); 9b(S,R) 5-(4-aminophenyl)-7-methoxy-2,3,4,4a,5,9b-hexahydro-1H-indeno[1,2-b]pyridine.
Melting point: 245° - 248° C (2 HCl)

EXAMPLE 43

4a(S,R); 5(R,S); 9b(S,R) 5-(4-aminophenyl)-7-hydroxy-2,3,4,4a,5,9b-hexahydro-1H-indeno[1,2-b]pyridine.
Melting point: 245° - 247° C (2 HCl)

EXAMPLE 44

4a(S,R); 5(R,S); 9b(S,R) 1-methyl-5-(4-aminophenyl)-2,3,4,4a,5,9b-hexahydro-1H-indeno[1,2-b]pyridine.
Melting point: 264° - 266° C (HCl)

EXAMPLE 45

4a(S,R); 5(R,S); 9b(S,R) 5-(4-methylphenyl)-7-hydroxy-2,3,4,4a,5,9b-hexahydro-1H-indeno[1,2-b]pyridine.
Melting point: 265° - 267° C (HCl)

EXAMPLE 46

4a(S,R); 5(R,S); 9b(S,R) 1-methyl-5-(4-methylphenyl)-7-hydroxy-2,3,4,4a,5,9b-hexahydro-1H-indeno[1,2-b]pyridine.
Melting point: 242° - 244° C (HCl).

EXAMPLE 47

4a(S,R); 5(S,R); 9b(S,R) 1-methyl-5-(2-fluorophenyl)-2,3,4,4a,5,9b-hexahydro-1H-indeno[1,2-b]pyridine.
Melting point: 216° C (HCl)

EXAMPLE 48

4a(S,R); 5(R,S); 9b(S,R)
5-phenyl-7-hydroxy-8-methoxy-2,3,4,4a,5,9b-hexahydro-1H-indeno[1,2-b]pyridine The compound was obtained in analogy to Example 14 from 5-phenyl-7,8-dimethoxy-2,3,4,4a,5,9b-hexahydro-1H-indeno[1,2-b]-pyridine.
Melting point: 197° - 200° C (HCl)

EXAMPLE 49

4a(S,R); 5(R,S);
5-(4n-butoxyphenyl)-2,3,4,4a,5,9b-hexahydro-1H-indeno[1,2-b]pyridine The compound was obtained in analogy to Example 14 from 4a(S,R); 5(R,S); 9b(S,R) 5-(4-fluorophenyl)-2,3,4,4a,5,9b-hexahydro-1H-indeno[1,2-b]pyridine.
Melting point: 102° - 194° C (HCl)

EXAMPLE 50

4a(S,R); 5(R,S); 9b(S,R)
1-methyl-5-(4-n-butoxyphenyl)-2,3,4,4a,5,9b-hexahydro-1H-indeno[1,2-b]pyridine The compound was prepared in analogy to Example 14 from 4a(S,R); 5(S,R); 9b(S,R) 1-methyl-5-(4-fluorophenyl)-2,3,4,4a,5,9b-hexahydro-1H-indeno[1,2-b]pyridine.
Melting point: 185° - 187° C (HCl)

EXAMPLE 51

4a(S,R); 5(R,S); 9b(S,R)
5-(3-n-butoxyphenyl)-2,3,4,4a,5,9b-hexahydro-1H-indeno[1,2-b]pyridine The compound was prepared in analogy to Example 14 from 4a(S,R); 5(R,S); 9b(S,R) 5-(2-fluorophenyl)-2,3,4,4a,5,9b-hexahydro-1H-indeno[1,2-b]pyridine.
Melting point: 166° - 168° C (HCl)

EXAMPLE 52

4a(S,R); 5(R,S); 9b(S,R)
5-(4-hydroxyphenyl)-2,3,4,4a,5,9b-hexahydro-1H-indeno[1,2-b]pyridine 0.01 mol of 4a(S.R); 5(R,S); 9b(S,R) 5-(4-n-butoxyphenyl)-2,3,4,4a,5,9b-hexahydro-1H-indeno[1,2-b]pyridine was heated in a mixture of 7 ml of hydrobromic acid in glacial acetic acid and 3.5 ml of 48% aqueous hydrobromic acid for 4 hours to 140° C. After cooling, water was added and the precipitated crystals were suction-filtered.
Melting point: 285° C (HBr)

As described in Example 52, the following three compounds were prepared from the corresponding butoxy compounds:

EXAMPLE 53

4a(S,R); 5(R,S); 9b(S,R) 5-(3-hydroxyphenyl)-2,3,4,4a,5,9b-hexahydro-1H-indeno[1,2-b]pyridine.
Melting point: 258° - 259° C (HBr)

EXAMPLE 54

4a(S,R); 5(R,S); 9b(S,R) 1-methyl-5-(4-hydroxyphenyl)-2,3,4,4a,5,9b-hexahydro-1H-indeno[1,2-b]pyridine.
Melting point: 255° - 257° C (HBr)

EXAMPLE 55

4a(S,R); 5(R,S); 9b(S,R) 1-methyl-5-(3-hydroxyphenyl)-2,3,4,4a,5,9b-hexahydro-1H-indeno[1,2-b]pyridine.
Melting point: 239° C (HCl)

EXAMPLE 56

4a(S,R); 5(R,S); 9b(S,R)
1-methyl-5-(4-methylphenyl)-7-methoxy-2,3,4,4a,5,9b-hexahydro-1H-indeno[1,2-b]pyridine 0.01 mol of 4a(S,R); 5(R,S); 9b(S,R) 1-methyl-5-(4-methylphenyl)-7-hydroxy-2,3,4,4a,5,9b-hexahydro-1H-indeno[1,2-b]pyridine was dissolved in 25 ml of methanol and a solution of 0.1 mol of diazomethane in 250 ml of ether was added. The solution was allowed to stand for 48 hours at room temperature, then it was concentrated and taken up in ether. The solution was extracted once with dilute sodium hydroxide solution, dried and concentrated.
Melting point: 65° - 73° C (HCl)

EXAMPLE 57

4a(S,R); 5(R,S); 9b(S,R)
1-methyl-5-(4-methoxyphenyl)-2,3,4,4a,5,9b-hexahydro-1H-indeno[1,2-b]pyridine The compound was prepared from the compound prepared according to Example 54 by reacting with diazomethane in analogy to Example 56.
Melting point: 227° - 229° C (HCl)

EXAMPLE 58

(a) 4a(S,R); 5(R,S); 9b(S,R)
1n-butyryl-5-phenyl-2,3,4,4a,5,9b-hexahydro-1H-indeno[1,2-b]pyridine 0.01 mol of 4a(S,R); 5(R,S); 9b(S,R) 5-phenyl-2,3,4,4a,5,9b-hexahydro-1H-indeno[1,2-b]pyridine was dissolved in 50 ml of pyridine to which 0.012 mol of butyryl chloride was added. After 24 hours, the solution was poured onto ice, extracted with ethyl acetate, dried and concentrated. The remaining oil was further worked in crude state.

(b) 4a(S,R); 5(R,S); 9b(S,R)
1-n-butyl-5-phenyl-2,3,4,4a,5,9b-hexahydro-1H-indeno[1,2-b]pyridine The compound was obtained by reduction of the compound synthesized under a) according to Example 1b.

| NMR spectrum: | CH—C | 4.5 (d) | J = 9 Hz; |
|---|---|---|---|
| | CH—N | 3.5 (d) | J = 5 Hz. |

The following are starting materials that have been prepared for Examples 2, 6, 7, 9, 11, 12 and 13:

| $R^1$ | $R^2$ | $R^3$ | Melting point |
|---|---|---|---|
| H | H | 4-$CH_3$—$C_6H_4$ | 195 - 198° C |
| $OCH_3$ | $OCH_3$ | 4-$NO_2$—$C_6H_4$ | 308 - 310° C |
| H | H | 3-$NO_2$—$C_6H_4$ | 226° C |
| H | H | 2-$CF_3$—$C_6H_4$ | 253 - 255° C |
| $OCH_3$ | $OCH_3$ | 3-pyridyl | 248 - 250° C |
| H | H | thienyl | 218 - 222° C |
| H | H | 4-$NO_2$-3-Cl—$C_6H_3$ | 288 - 291° C |
| H | H | 3-$CH_3$—$C_6H_4$ | 215° C |
| H | H | 2-$CH_3$—$C_6H_4$ | 215° C |
| H | $OCH_3$ | 4-$NO_2$—$C_6H_4$ | 245 - 250° C |
| H | Cl | 4-$NO_2$—$C_6H_4$ | 234 - 236° C |
| H | $OCH_3$ | 4-$CH_3$—$C_6H_4$ | 211 - 214° C |
| H | H | 2-F—$C_6H_4$ | 218 - 220° C (decomposition) sintering beginning at 200° C |
| H | H | 4-F—$C_6H_4$ | 215 - 218° C (decomposition) sintering beginning at 190° C |

| $R^1$ | $R^2$ | $R^3$ | Melting point: |
|---|---|---|---|
| H | H | 4-$CH_3$—$C_6H_4$ | 231 - 233° C |
| $OCH_3$ | $OCH_3$ | 4-$NH_2$—$C_6H_4$ | 268 - 270° C |
| H | H | 3-$NH_2$—$C_6H_4$ | 230 - 232° C |
| H | H | 2-$CF_3$—$C_6H_4$ | 194 - 197° C |
| $OCH_3$ | $OCH_3$ | 3-pyridyl | 229 - 232° C |
| H | H | thienyl | 197 - 199° C |
| H | H | 4-$NH_2$-3-Cl—$C_6H_3$ | 267 - 271° C |
| H | H | 3-$CH_3$—$C_6H_4$ | 189 - 191° C |
| H | H | 2-$CH_3$—$C_6H_4$ | 219 - 220° C |
| H | $OCH_3$ | 4-$NH_2$—$C_6H_4$ | 221 - 223° C |
| H | Cl | 4-$NH_2$—$C_6H_4$ | 212 - 216° C |
| H | $OCH_3$ | 4-$CH_3$—$C_6H_4$ | 211 - 213° C |
| H | H | 2-F—$C_6H_4$ | 203 - 204° C |
| H | H | 4-F—$C_6H_4$ position | 240 - 245° C (decomposition) |

What is claimed is:
1. 4a(S,R); 5(R,S); 9b(S,R) 5-(4-aminophenyl)-2,3,4,4a,5,9b-hexahydro-1H-indeno[1,2-b]pyridine.
2. A pharmaceutical composition for the treatment of depression, which composition comprises a compound as in claim 1 in combination with a pharmaceutical carrier.
3. The method of treating depression in a patient suffering therefrom which comprises an anti-depressively effective amount of administering to said patient an anti-depressively effective amount of a compound as in claim 1.

* * * * *